US011124848B2

(12) United States Patent
Geraats et al.

(10) Patent No.: US 11,124,848 B2
(45) Date of Patent: Sep. 21, 2021

(54) SPECIES OF TOBAMOVIRUS

(71) Applicant: NUNHEMS B.V., Nunhem (NL)

(72) Inventors: Bart Peter Johan Geraats, Weert (NL); Marco Antonio Mammella, Bologna (IT); Massimo Turina, Turin (IT); Marina Ciuffo, Moncalieri (IT)

(73) Assignee: NUNHEMS B.V., Nunhem (NL)

( * ) Notice: Subject to any disclaimer, the term of this patent is extended or adjusted under 35 U.S.C. 154(b) by 3 days.

(21) Appl. No.: 15/745,340

(22) PCT Filed: Jul. 13, 2016

(86) PCT No.: PCT/EP2016/066643
§ 371 (c)(1),
(2) Date: Jan. 16, 2018

(87) PCT Pub. No.: WO2017/012951
PCT Pub. Date: Jan. 26, 2017

(65) Prior Publication Data

US 2018/0208628 A1 Jul. 26, 2018

(30) Foreign Application Priority Data

Jul. 17, 2015 (EP) .................................... 15177316

(51) Int. Cl.

| | |
|---|---|
| ***C12Q 1/70*** | (2006.01) |
| ***C07K 14/005*** | (2006.01) |
| ***C07K 16/10*** | (2006.01) |
| ***C12N 7/00*** | (2006.01) |
| ***G01N 33/50*** | (2006.01) |

(52) U.S. Cl.
CPC ............ *C12Q 1/701* (2013.01); *C07K 14/005* (2013.01); *C07K 16/10* (2013.01); *C12N 7/00* (2013.01); *G01N 33/5097* (2013.01); *C12N 2770/00021* (2013.01); *C12N 2770/00022* (2013.01); *C12N 2770/00031* (2013.01)

(58) Field of Classification Search
None
See application file for complete search history.

(56) References Cited

U.S. PATENT DOCUMENTS

| | | | |
|---|---|---|---|
| 2007/0234441 A1 | 10/2007 | Allersma et al. | |
| 2011/0185451 A1 | 7/2011 | Allersma et al. | |
| 2014/0033357 A1 | 1/2014 | De Bloois | |

FOREIGN PATENT DOCUMENTS

| | | |
|---|---|---|
| WO | WO 2006/038794 A2 | 4/2006 |
| WO | 2018219941 A1 | 12/2018 |
| WO | 2020018783 A1 | 1/2020 |

OTHER PUBLICATIONS

Moreira et al Brazilian Phytopathology (Fitopatol. bras.) 28 (6): 1-10, Nov./Dec. 2003, translation from Portuguese to English (Year: 2003).*
Sequence Accession HE818452, May 21, 2012 (Year: 2012) attached at the end of the office action.*
Alishiri et al., “Prevalence of Tobacco mosaic virus in Iran and Evolutionary Analyses of the Coat Protein Gene,” Plant Pathology Journal, 2013, vol. 29, No. 3, pp. 260-273.
GenBank Accession No. FR878069.1, “Tobacco mosaic virus strain *Ohio v*, complete genome, genomic RNA,” http://www.ncbi.nih.gov/nuccore/FR878069, last updated date Jan. 10, 2012 (4 pages).
Henikoff et al., “Amino acid substitution matlices from protein blocks”, PNAS, 1992, vol. 89, pp. 10915-10919.
International Search Report and Written Opinion issued in International Application No. PCT/EP2016/066643, dated Sep. 22, 2016 (9 pages).
ISF, Method for the detection of infectious tobamoviruses on tomato seed, 2017 www.worldseed.org/cms/medias/file/TradeIssues/PhytosanitaryMatters/SeedHealthTesting/ISHI-Veg/Tom 2 pages.
Ishibashi et al., “The Resistance Protein TM-1 Inhibits Formation of a Tomato Mosaic Virus Replication Protein-Host Membrane Protein Complex,” J Virol. Jul. 2013; vol. 87, No. 14, pp. 7933-7939.
King et al. “Virus Taxonomy: 9th report of the International Committee on Virus Taxonomy”, ISBN 978-0-12-384684-6, 2012, pp. 1155-1156 (4 pages total).
Moreira et al., “Characterization of a new Tomato mosaic virus strain isolated from tomato in the State of Sao Paulo, Brazil,” 2003, http://www.scielo.br/scielo.php?script=sci_arttext&pid=S0100-41582003000600004, pp. 1-11.
Weber et al., “Tm-22 Resistance in Tomato Requires Recognition of the Carboxy Terminus of the Movement Protein of Tomato Mosaic Virus,” MPMI, 1998, vol. 11, No. 6, pp. 498-503.
“Alignment of genomic sequence of sample 2015-406 with SEQ ID No. 1 of EP 3325502 B1”, submitted in opposition to EP 3325502, Mar. 2021, pp. 1-5.
“Alignment of KT383474 with SEQ ID No. 1 of EP 3325502 B1”, submitted in opposition to EP 3325502, Mar. 2021, pp. 1-5.
“Alignment of KX619418 with SEQ ID No. 1 of EP 3325502 B1”, submitted in opposition to EP 3325502, Mar. 2021 pp. 1-6.
“Alliance Seed, Tomato—Candela F1”, Product sheet of Candela, submitted in opposition to EP 3325502, Mar. 2021, 1 page.
“Annual Title Page—Listing of Frameworks by Funder—Approved Budget”, Agricultural Research Organization, Volcani enter, Funding Source File No. 20-10-0070, Dec. 28, 2016, 1 page (submitted in opposition to EP 3325502).
“Call for Submission of New Research Proposals for 2016 in the Agriculture and Rural development sector”, submitted in opposition to EP 3325502, Mar. 2021, pp. 1-6.
Comparison of MS838349 (=SEQ ID from WO 2017/012951) with KX619418 and Comparison of MS838349 (=SEQ ID from WO 2017/012951) with KT383474), submitted in opposition to EP 3325502, Mar. 2021, pp. 1-14.

(Continued)

*Primary Examiner* — Elizabeth F McElwain
(74) *Attorney, Agent, or Firm* — Arent Fox LLP

(57) ABSTRACT

The present invention provides a new species of tobamovirus and its use to identify plants comprising resistance against the virus.

21 Claims, 3 Drawing Sheets

Specification includes a Sequence Listing.

(56) References Cited

OTHER PUBLICATIONS

"Confirmation of Research Commencement", State of Israel Ministry of Agriculture & Rural Development, Research Plan No. 261115918/20-10-0070, Nov. 2, 2017, 1 page (submitted in opposition to EP 3325502).
NCIMB Accession No. KX619418, "Sequence database NCBI of sequence of Israel virus 01", NCBI database, dated Nov. 13, 2016, 1 page (submitted in opposition to EP 3325502).
NCIMB Accession No. KT383474, "Sequence database NCBI of sequence of Jordan virus 03", NCBI database, dated Nov. 29, 2015, 1 page (submitted in opposition to EP 3325502).
"Declaration of Dr. Aviv Dombrovsky, employee of Agricultural Research Organization(ARO), The Volcani Center", submitted in opposition to EP 3325502, Feb. 28, 2021, pp. 1-6.
"Declaration of Abdullah Ahmad Sa'sa, Employee of Rijk Zwaan", submitted in opposition to EP 3325502, Mar. 16, 2021, pp. 1-4.
"Declaration of Daniel Ludeking, employee of Rijk Zwaan", submitted in opposition to EP 3325502, Mar. 16, 2021, pp. 1-6.
"Declaration of Dr. Moshe Lapidot, employee of the Agricultural Research Organisation (ARO), The Volcani Center", submitted in opposition to EP 3325502, Mar. 1, 2021, pp. 1-5.
"Declaration of Hamzeh Zuhdi Flabboub, employee of Rijk Zwaan", submitted in opposition to EP 3325502, Mar. 16, 2021, pp. 1-4.
"Email of Enza Zaden on sequencing of AE50 isolate Saudi Arabia", Jun. 2015, 1 page (submitted in opposition to EP 3325502).
"Email of University of Amsterdam to Enza Zaden to confirm that sequencing of the virus was finished", Jul. 8, 2015, 1 page (submitted in opposition to EP 3325502).
"Email string Enza Zaden on virus availability from Jan. to Jun. 2015", pp. 1-4 (submitted in opposition to EP 3325502).
"Fedex Airway bill 1", May 10, 2015, 1 page (submitted in opposition to EP 3325502).
"Fedex Airway bill 2", Jul. 9, 2015, 1 page (submitted in opposition to EP 3325502).
"Field and Vegetables—The Professional Magazine of the Vegetables Industry", Vegetables Bulletin—Field and Vegetables, No. 285, Oct. 2015, pp. 1-9.
"Genus: Tobamovirus", Positive-Sense RNA Viruses—Virgaviridae, International Committee on Taxonomy of Viruses (ICTV) Reports, Feb. 8, 2021, pp. 1-6.
"Letter of Declaration—Dr. Dekker", University of Amsterdam, submitted in opposition to EP 3325502, Mar. 16, 2021, pp. 1-7.
"Open Call—Request for Proposals for 2016—For submitting proposals in the field of agriculture and rural levelopment", Volcani Institute Israel, Dec. 31, 2014, pp. 2-29 (submitted in opposition to EP 3325502).
"Report of University of Amsterdam on sequencing new ToMV virus", Jul. 2015, pp. 1-5 (submitted in opposition to EP 3325502).
"Request of a Research Grant—Temporary ID code 0781-003", Bureau of the Chief Scientist, The Ministry of Agriculture and Rural Development, May 18, 2015, pp. 1-3 (submitted in opposition to EP 3325502).
"Research Proposal 20-10-0070", State of Israel, Ministry of Agriculture, Rural Development & Chief Scientific Office, Oct. 6, 2015, 1 page (submitted in opposition to EP 3325502).
"Run report of sequencing project performed by University of Amsterdam on new virus isolate", Jul. 7, 2015, pp. 1-5 (submitted in opposition to EP 3325502).
"Screenshot of database transcript of Enza Zaden date of receipt of virus isolated from Jordan and Saudi Arabia", submitted in opposition to EP 3325502, Mar. 2021, 1 page (submitted in opposition to EP 3325502).
"Screenshot of the FASTA file created by the University of Amsterdam on 13th of Jul. 2015 on the virus genome sequence", 1 page (submitted in opposition to EP 3325502).
"Sequence alignments of KX619418 and KT383474 against SEQ ID No. 1", submitted in opposition to EP 3325502, Mar. 2021, pp. 1-14.
GenBank Accession No. KT383474.1, "Tomato brown rugose fruit virus isolate Tom1-Jo, complete genome", May 26, 2016, pp. 1-4.
GenBank Accession No. KX619418.1, "Tomato brown rugose fruit virus—israeli isolate TBRFV-IL, complete genome", May 23, 2017, pp. 1-3.
"UPS Airway bill 3", Jul. 7, 2015, 1 page (submitted in opposition to EP 3325502).
"Guidelines for the conduct of tests for distinctness, uniformity and stability—Tomato (UPOV Code SOLAN_LYC, Solanum Lycopersicum L.)" UPOV, International Union for the Protection of New Varieties of Plants, Geneva, TG/44/11, Oct. 20, 2011, pp. 1-71.
"Partial Revision of the Test Guidelines for Sweet Pepper, Hot Pepper, Paprika, Chili (Document TG/76/8)—Technical Committee, Fifty First Session" UPOV, International Union for the Protection of New Varieties of Plants, Geneva, TC/51/30, Mar. 5, 2015, pp. 1-25.
A. TH. B. Rast, "Variability of tobacco mosaic virus in relation to control of tomato mosaic in glasshouse tomato crops by resistance breeding and cross protection", Institute of Phytopathological Research, Wageningen, Jun. 6, 1975, pp. 1-76.
Gantz, et al., "National Conference on Edible Tomatoes", Jun. 30, 2015, 1 page.
Gantz, et al., "Warning of TMV and ToMV in Tomatoes", Ministry of Agriculture and Rural Development, Jan. 2015, pp. 1-4.
Ganz, et al., "Coping with Tomato Tobamoviruses", The Ministry of Agriculture and Rural Development, Nov. 2014, pp. 1-4.
Ganz, et al., "TMV and ToMV Tomato Viruses Alert", The Ministry of Agriculture and Rural Development, Jan. 2015, pp. 1-4.
Hudcovicova, et al., "Molecular Selection of Tomato and Pepper Breeding Lines Possessing Resistance Alleles Against Tobamoviruses", Agriculture/Pol'nohospodárstvo, vol. 61, Issue 1, Apr. 27, 2015, pp. 33-37.
Lanfermeijer, et al., "The products of the broken Tm-2 and the durable Tm-22 resistance genes from tomato differ in four amino acids", Journal of Experimental Botany, vol. 5, Issue 421, Nov. 2005, pp. 2925-2933.
Letschert, et al., "Detection and differentiation of serologically cross-reacting tobamoviruses of economical importance by RT-PCR and RT-PCR-RFLP", Journal of Virological Methods, vol. 106, Issue 1, Oct. 2002, pp. 1-10.
Li, et al., "Complete Genome Sequence of a New Tobamovirus Naturally Infecting Tomatoes in Mexico", Genome Announcements, vol. 1, Issue 5, Sep./Oct. 2013, pp. 1-2.
Luria, et al., "A New Israeli Tobamovirus Isolate Infects Tomato Plants Harboring Tm-22 Resistance Genes", PloS one, vol. 12, Issue 1, Jan. 20, 2017, pp. 1-19.
Maayan et al., "Using genomic analysis to identify tomato Tm-2 resistance-breaking mutations and their underlying evolutionary path in a new and emerging tobamovirus", Archives of Virology, vol. 163, Issue 7, Mar. 27, 2018, pp. 1863-1875.
Moya, et al., "The population genetics and evolutionary epidemiology of RNA viruses", Nature Reviews Microbiology, vol. 2, Issue 4, Apr. 1, 2004, pp. 279-288.
Panthee, et al., "Novel molecular marker associated with Tm2a gene conferring resistance to tomato mosaic virus in tomato", Plant Breeding, vol. 132, Issue 4, May 29, 2013, pp. 413-416.
Salem, et al., "A new tobamovirus infecting tomato crops in Jordan", Archives of Virology, vol. 160, Issue 12, Dec. 2015, pp. 1-6.

* cited by examiner

Figure 1 – genome sequence of strain VE484 (SEQ ID NO: 1)

gtatttttgttttacaacatataccaacaacaacaaacaacaaacaacaacattacaattacta
tttacaactacaatggcatacacacagacagctaccacatccgctttgctcgacactgtccgag
gtaacaataccttggtcaatgatcttgcgaagcggcgtctttatgacacagcggtcgacgagtt
caacgctcgtgatcgcaggcccaaagtaaattttccaaagtaataagtgaggaacagacgctt
attgctactagggcatatccagaattccagataaccttctataatacgcagaacgccgtgcatt
cgcttgccggtggactacgatccttagaactggaatatctaatgatgcagatcccgtacggatc
actcacatatgatataggtgggaattttgcatctcatctgttcaaaggacgggcatatgttcac
tgctgtatgcccaatcttgatgtccgcgacataatgcggcacgaaggccagaaagacagtatag
aattatacctttccaggcttgagcggggcaacaaagttgtcccaaatttccaaaaggaagctct
tgacagatacgctgaaacgccagacgaagttgtctgtcacagtaccttccaaacgtgtacgcac
cagcaggtggaaaacacaggcagggtgtatgctattgcattgcacagtatatacgatatacctg
ctgatgaattcggagcggcacttttaaggaaaaatgtccatgtttgttacgccgccttccactt
ttccgagaatttacttctcgaagattcacacgtcaaccttgacgaaatcaacgcgtgtttttcg
cgtgatggagacaagctgactttttctttcgcatctgagagcactttaaattattgtcatagtt
attctaatattttaaaatacgtgtgcaaaacttacttcccggcatctaatagagaggtctacat
gaaggagtttttggtcaccagggttaacacctggttttgtaagttttctaggatagatactttt
ttattatacaaggggggtagcccacaaaggtgtaaatagtgagcaattttacagcgcaatggaag
atgcatggcactacaaaaagactcttgcaatgtgtaacagcgagaggattcttcttgaagattc
ctcatcggtcaattactggttcccaaaaatgagagatatggtcatagttcctctattcgacata
tctctcgacaccagtaaaaggacccgcaaagaagtcttagtgtcaaaggattttgtattcacag
ttttaaatcacattcgcacttatcaagccaaggcacttacatactccaatgttttatcctttgt
cgaatcaattcgttcaagggtaattatcaacggagtgactgccaggtctgagtgggatgttgac
aaatctcttttgcaatccttgtccatgacatttttcttgcatactaagcttgccgttttaaaag
acgaattgttaatcagcaagtttagtttggggccaaaatcagtaagccagcatgtatgggatga
gatttccctggcttttggaaacgcatttccatcgatcaaggagagactgctaaatcggaaacta
attaaagtgtcgggagacgcattagaaatcagggtgcctgatttatatgtgacttttcacgata
gattagtgactgagtacaaaacatcggtggatatgccagtgcttgatatcagaaagagaatgga
ggagactgaggttatgtacaatgcattgtctgagctatctgtgctcaaggagtcggacaagttc
gacgctgatgtttttttcccggatgtgccagactttggaggtagacccaatgactgcagcaaagg
ttattgtggcagtgatgagcaacgagagcggactgactcttacattcgaacagccaactgaagc
aaatgtcgcattggcacttaaagattcagaaaaagcctctgagggtgcactagtggttacttct
agagatgttgaagaaccatccatgaagggttcaatggcaagaggagagttacaattggccggtc
tgtctggagaccaaccagagtcttcctatactcggaacgaggaaatagagtcattagagcaatt
ccacatggcaacggctagttcgttaattcggaaacagatgagttcgattgtgtacacgggcccc

Figure 1 (continued)

attaaagttcagcaaatgaaaaactttattgatagcctggtagcatcactctctgctgcggtgt
cgaacctagtcaagatcctaaaggatacagctgctatagatctcgaaacccgtcagaagtttgg
agtcttagatgttgcgaccaaaagatggttaattaaacctttagccaagaatcacgcatggggc
gttattgaaacacatgctaggaagtaccacgttgcacttttggagtatgatgagcatggagtgg
taacttgcgacagttggagaagggtggccgtgagttctgagtcaatggtttattctgatatggc
gaagctcagaacactgaggagattattaagagatggtgagcctcatgtcagcagtgctaaagtc
gtcctagttgacggtgtcccgggttgtggaaagacaaaagagattctctcgaaagtaaatttg
aggaagatctaatcttagtaccgggtaagcaggctgctgaaatgataaagaggcgtgctaatgc
gtcaggaataattcaagccacaagagataatgttcgtactgttgattcatttataatgaattac
ggtaaaggaacacgctgtcagttcaaaggttatttatcgacgaaggtctgatgttgcacactg
gttgtgtgaattttcttgtttctatgtctctgtgcgaaattgcatatgtttatggagacacaca
acaaattccatacatcaacagagtatccggttttccgtaccctgcacattttgcaaaaatagag
gttgatgaggtggaaactcgcagaactacgctgcgttgtccagccgacattacccactatctta
acagaaggtacgaaggatatgtcatgtgtacatcgtcggttaaaaagtcagtttctcaggaaat
ggtgagcggggccgcaatgatcaatcctgtatctaagccattgaatgggaaagttttgactttc
actcagtctgataaagaggcgctgctttctcgaggatatacggacgtccatacagtacatgagg
tacaaggtgagacatatgcagatgtgtcgttggtcagattgactccgacacctgtatctatcat
cgcaggagatagtccgcacgttctcgtagctttgtcaaggcatacccaaacattgaagtattac
accgtagtgatggatcctcttgtaagtataattagggatttagaaaaacttagttcttacttgt
tagatatgtataaagtagatgcagggacccaatagcaattacaggtagactccgtgtttaaagg
ttctaatctttttgttgcagcaccaaagactggagatatctcagatatgcaattttactatgat
aagtgtctcccaggtaatagcaccatgttaaataactatgatgctgttaccatgaggttgactg
acatttctcttaatgtcaaagattgcatattggatttctctaagtctgtggctgcaccgaagga
tccgatcaaaccactgattccaatggtacgaacagcggcagaaatgccacgccagactggacta
ttggaaaatttggtggcgatgatcaaaagaaactttaattcaccggagttatcaggaataatcg
acattgagaatactgcatctttagtagtagataaatttttgatagttacttgcttaaagaaaa
aagaaaaccaaataaaaatgtttctttattttgtagagagtctctcaatagatggttagagaag
caggagcaagtgaccattggtcagcttgcagattttgattttgtggatcttcctgccgttgatc
agtacaggcatatgattaaagcgcaacctaagcagaagctggatacatcaattcaaagcgaata
tccggccttgcagacgattgtgtatcattcgaaaaagatcaacgcaatcttcggtcctttgttc
agtgagctcacaaggcaaatgctcgaaagcatagactcaagtaagtttttgttctttacaagga
agacgccagctcaaattgaggatttcttcggagatctcgatagccatgtccctatggatatctt
ggagttggatatttcgaagtatgacaaatctcagaacgagttccactgtgcagtagagtatgaa
atatggagaagacttggattagaagattttctgggagaagtttggaaacaaggccataggaaaa
ctactcttaaagattacacagctggtattaaaacgtgtttatggtaccagagaaagagtgggga

Figure 1 (continued)

cgttacaacattcatcggtaatacggtgattattgctgcttgtttagcttccatgttgcccatg
gagaaaataatcaaaggtgcattttgcggagatgacagtttactatacttcccaaaaggttgtg
agtttcctgacatacagcatacagccaaccttatgtggaatttcgaggctaagctattcagaaa
gcagtatggttatttctgtggaaggtacgtgatacatcatgacagagggtgtattgtttattat
gaccctttgaagttgatttctaaacttggtgctaaacacatcaaggattgggatcacttagaag
agttcagaagatccctttgtgatgttgcaaattcgttgaacaactgtgcgtattacacgcagtt
ggacgacgctgtgagtgaggtccataaaaccgcacccccgggttcgtctgtatataaaagttta
gttaaatatctgtccgataaggttctttttagaagtttgtttatagatggctcttgttaagggt
aaagtcaatattaatgagttcatagacttgtcaaaatcagaaaaatttcttccgtctatgttca
cacctgttaagagtgtcatgatctccaaggttgataagatattggttcatgaagatgaatcttt
gtccgaagtcaatttactcaaaggtgtaaaactcattgatggtggctatgtacatcttgctggt
cttgtggtgacaggtgaatggaatttgccagataattgtcgtggtggtgtcagtgtctgtttgg
tcgataagagaatggagagagcggacgaggcaactcttgcttcatactataccgcagcggctaa
gaaaaggtttcagttcaaagtcgttccaaattacaacatcactaccaaggacgcagaaaaggca
gtttggcaagtactagttaatattagaaatgttaaaattgctgcgggttactgtccgctgtcat
tagaatttgtgtcagtgtgtattgtttataaaaatattataaaactcggtttgagagagaaaat
tacgagcgtcacggatggagggcccatggaactatcagaagaagttgttgatgagttcatggaa
gaagtcccgatgtctgtaaggcttgcaaaatttcgttcgaagaccggaaaaaagtttagtagta
aaagtgagaataatagtggtaataataggccgaaaccagacaaaaaccaaaggaagggaaaggg
tttaaaagttagggttgagaaggataatttaattgataatgaattggagacttacgtcgccgat
tcagattcgtattaaatatttaaatatgtcttacacaatcgcaactccatcgcaatttgtgttt
ttgtcatcagcatgggccgaccctatagaattaataaatttatgtactaattcactaggtaatc
agttccaaacacaacaagctagaacaaccgttcaacggcaatttagcgaagtgtggaaacctgt
ccctcaagtcactgttaggtttcctgacagtggttttaaggtgtataggtacaatgcggtacta
gatcctctagttactgctttgttaggagctttcgatactagaaataggattatagaagtcgaaa
atcaggcgaacccgacaaccgccgaaacgttagacgctactcgtagagtagatgacgcaacggt
ggctataaggagcgctataaataatttagtagtagaattggtcaaaggaacaggtttgtacaat
cagagcacatttgaaagtgcatccggtttacaatggtcctctgcacctgcatcttgagataatc
gagatgcttaaataacagattgtgtctgcaaacacacgtggtacgtacgataacgtatagtgtt
tttccctccacttaaatcgaagggtagtgtcttggagcgcgcgggacaaatgtgtatggttcat
acacatccgtaggcacgtaataaagcgagggattcgaattcccccggaacccccggtaggggcc
ca

SPECIES OF TOBAMOVIRUS

CROSS REFERENCE TO RELATED APPLICATIONS

This application is a 35 U.S.C. 371 National Phase of PCT Application No. PCT/EP2016/066643 filed Jul. 13, 2016, which claims benefit to EP Application No. 15177316.5 filed Jul. 17, 2015, the disclosure of which is hereby incorporated by reference in its entirety.

FIELD OF THE INVENTION

The invention relates to a new species of the genus tobamovirus (family Virgaviridae), which infects Solanaceae plants. The invention also relates to the use of the virus species for identifying and/or generating resistant Solanaceae plants, such as tomato, tobacco, pepper and eggplant. The new tobamovirus species is able to multiply and spread on tomato plants which carry Tomato Mosaic Virus (ToMV) resistance genes Tm1, Tm2 and $Tm2^2$, i.e. these resistance genes are ineffective against the new virus and plants develop various symptoms when infected, such as (mild) mosaic on leaves, bronzing of leaves, blistering and leaf distortions. Provided is a new virus species, called herein Tomato Mosaic Severe Virus (ToMSV or TMSV), methods for diagnosing the presence of the new tobamovirus species in plants and/or plant parts of Solanaceae species (especially tomato, tobacco, pepper and eggplant) and methods for using isolates of the new virus, such as isolate VE484 (deposited on Jan. 19, 2015 under accession number DSM 29970), to screen plants and/or plant parts for resistance against the virus.

BACKGROUND OF THE INVENTION

Tobamoviruses in tomato were historically classified together as strains of Tobacco Mosaic Virus (TMV). However, nowadays these tobamoviruses are classified as different virus species based on sequence dissimilarity. Species of tobamoviruses include Pepper Mild Mottle Virus (PMMV), Tobacco Mosaic Virus (TMV), Tomato Mosaic Virus (ToMV), and many others (see e.g. ICTVdB Index of Viruses).

Plant viruses can be devastating to production of fruits and vegetables. Although many commercial varieties carry virus resistance genes, such resistance genes can become ineffective, as resistance breaking strains of a species may evolve or as new virus species may evolve. In tomato, three dominant ToMV resistance genes have been used for decades to control ToMV, namely Tm1 (introgression from *S. habrochaites*; conferring resistance to ToMV strains 0 and 2), Tm2 and $Tm2^2$ (both introgressions from *S. peruvianum*, conferring resistance against ToMV strains 0 and 1, and 0, 1 and 2, respectively). The Tm1 resistance gene encodes a protein that binds ToMV replication proteins and inhibits the RNA-dependent RNA replication of ToMV. The replication proteins of resistance-breaking mutants of ToMV do not bind Tm1, indicating that the binding is important for inhibition (see Ishibashi and Ishikawa, J Virol. July 2013; 87(14): 7933-7939). The $Tm2^2$ resistance gene encodes a protein that recognizes the ToMV movement protein, especially the carboxyterminus of the movement protein, and $Tm2^2$ resistance breaking strains with amino acid changes in the carboxyterminus of the movement protein are not recognized anymore and can thereby overcome resistance (see Weber and Pfitzner, 1998, MPMI Vol 11, pp 498-503). There is a constant evolutionary race between resistance genes and virus evolution. It is therefore important to identify new viruses quickly, in order to have tools to identify resistance genes which are effective against such new viruses.

It is an object of the invention to identify a new species of tobamovirus, referred herein as Tomato Mosaic Severe Virus (ToMSV or TMSV), which can infect tomato plants carrying any of these three resistance genes or combinations thereof. It is also an object of the invention to provide methods for diagnosing this new virus species, as well as methods of using virulent isolates of the species to screen germplasm for new resistance sources.

BRIEF DESCRIPTION OF THE FIGURES

FIG. 1 shows the genome sequence of strain VE484 (SEQ ID NO: 1).

DETAILED DESCRIPTION OF THE INVENTION

As used herein, the term "to comprise" and its conjugations is used in its non-limiting sense to mean that items following the word are included, but items not specifically mentioned are not excluded. Nevertheless, the skilled person will understand that the term "comprise" also encompasses the term "consists". In addition, reference to an element by the recitation of "a" or "an" does not exclude the possibility that more than one of the element is present, unless the context clearly requires that there be one and only one of the elements. Thus, "a" or "an" usually means "at least one" or "one or more".

The term "cultivar" (or "cultivated" plant) is used herein to denote a plant having a biological status other than a "wild" status, which "wild" status indicates the original non-cultivated, non-domesticated, or natural state of a plant or accession, and the term cultivated does not include such wild, or weedy plants. The term cultivar does include material with good agronomic characteristics, such as breeding material, research material, breeding lines, elite breeding lines, synthetic population, hybrid, founder stock/base population, inbred lines, cultivars (open pollinated of hybrid cultivar), segregating population, mutant/genetic stock, and advanced/improved cultivar. In one embodiment the term cultivar also includes landraces, i.e. pepper plants (or populations) selected and cultivated locally by humans over many years and adapted to a specific geographic environment and sharing a common gene pool. Cultivars have good agronomic properties compared to wild accessions such as high yielding, bigger fruit size, higher fertility, higher uniformity of plants and/or fruits, etc.

As used herein, the term "plant" includes the whole plant or any parts or derivatives thereof, such as plant organs (e.g., harvested or non-harvested fruits, leaves, seed, flowers, etc.), plant cells, plant protoplasts, plant cell or tissue cultures from which whole plants can be regenerated, plant calli, plant cell clumps, and plant cells that are intact in plants, or parts of plants, such as embryos, pollen, ovules, ovaries, fruits (e.g., harvested tissues or organs, such as harvested pepper fruits or parts thereof), flowers, leaves, seeds, clonally propagated plants, roots, root-stocks, stems, root tips and the like. Also any developmental stage is included, such as seedlings, immature and mature, etc.

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one locus or gene (or a series of phenotypical characteristics due to this single locus or gene), but which can otherwise differ from one another enormously as regards the other loci or genes.

Solanaceae refers to a family of plants, which include genera (especially the genus *Solanum* and the genus *Capsicum*) that comprise fruit and vegetable species which are cultivated and bred by humans, such as e.g. *Solanum lycopersicum* (tomato), *Capsicum annuum* (peppers), *Solanum melongena* (aubergine) and *Solanum muricatum* (pepino).

"Tomato plants" or "cultivated tomato plants" are plants of the *Solanum lycopersicum*, i.e. varieties, breeding lines or cultivars of the species *Solanum lycopersicum*, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example wild accessions or wild relatives of a species. In one aspect of the invention so-called heirloom tomato varieties or cultivars, i.e. open pollinated varieties or cultivars commonly grown during earlier periods in human history and often adapted to specific geographic regions, are in one aspect of the invention encompassed herein as cultivated tomato plants. In one embodiment the term cultivar also includes landraces, i.e. plants (or populations) selected and cultivated locally by humans over many years and adapted to a specific geographic environment and sharing a common gene pool.

The term "cultivar" (or "cultivated" plant) is used herein to denote a plant having a biological status other than a "wild" status, which "wild" status indicates the original non-cultivated or natural state of a plant or accession, and the term cultivated does not include such wild, or weedy plants. The term cultivar does include material with good agronomic characteristics, such as breeding material, research material, breeding lines, elite breeding lines, synthetic population, hybrid, founder stock/base population, inbred lines, cultivars (open pollinated of hybrid cultivar), segregating population, mutant/genetic stock, and advanced/improved cultivar.

Wild relatives of tomato include *S. arcanum, S. chmielewskii, S. neorickii* (=*L. parviflorum*), *S. cheesmaniae, S. galapagense, S. pimpinellifolium, S. chilense, S. corneliomulleri, S. habrochaites* (=*L. hirsutum*), *S. huaylasense, S. sisymbriifolium, S. peruvianum, S. hirsutum, S. pennellii, S. lycopersicoides, S. sitiens* or *S. ochranthum.*

As used herein, "pepper plant" or "pepper" is a plant of genus *Capsicum* or parts thereof (e.g. fruits). Pepper includes all kinds of peppers, such as hot/pungent peppers and non-pungent peppers (sweet pepper). The term encompasses wild accessions and domesticated peppers.

"Domesticated pepper" refers to the species *Capsicum annuum* L., *Capsicum chinense* Jacq., *Capsicum frutescens* L., *Capsicum baccatum* L., and *Capsicum pubescens* Ruiz & Pay. The term "cultivated pepper" refers to breeding lines and varieties of domesticated pepper, which is cultivated by humans in the field or in protected environments (e.g. greenhouse or tunnels) for fruit production. Cultivars have good agronomic properties compared to wild accessions such as high yielding, bigger fruit size, higher fertility, higher uniformity of plants and/or fruits, etc. Examples of cultivars include cultivated varieties that belong to the species *Capsicum annuum, Capsicum chinense, Capsicum frutescens, Capsicum baccatum* and *Capsicum pubescens.*

A "plant genotype" refers to plants that are genotypically closely related, such as plants of an accession of a seed-bank (e.g. in the GRIN collection of the USA; http://www.ars-grin.gov/npgs/acc/acc_queries.html or the CGN (Centre for Genetic Resources) collection of Wageningen University and Research Centre in the Netherlands) and progeny thereof obtained by selfing, or plants of a plant line, or a plants of a variety.

A "plant line" or "breeding line" refers to a plant and its progeny. As used herein, the term "inbred line" refers to a plant line which has been repeatedly selfed.

"$F_1$, $F_2$, etc." refers to the consecutive related generations following a cross between two parent plants or parent lines. The plants grown from the seeds produced by crossing two plants or lines is called the $F_1$ generation. Selfing the $F_1$ plants results in the $F_2$ generation, etc. "$F_1$ hybrid" plant (or $F_1$ hybrid seed) is the generation obtained from crossing two inbred parent lines.

"Hybrid" or "hybrid plant" is a plant produced by the intercrossing (cross-fertilization) of at least two different plants or plants of different parent lines. It is understood that the seeds of such a cross (hybrid seeds) are encompassed herein, as well as the hybrid plants grown from those seeds and plant parts derived from those grown plants.

The term "trait" refers to a heritable characteristic, such as ToMSV resistance, which is transferable, e.g., by crossing and selection from one plant to another.

"ToMSV", "ToMSV strains" or "ToMSV isolates" or "ToMSV pathotypes" refers to strains of Tomato Mosaic Severe Virus which can be determined serologically (using antibodies), by microscopy, by sequence comparison, and/or by disease assays, all as described herein.

"VE484" refers to a virulent strain of ToMSV, a representative sample of which has been deposited at the DSZM under Accession number DSM29970.

"Tm1 gene" or "Tm1 resistance gene" refers to the dominant resistance gene as known in the art, conferring resistance to ToMV strains 0 and 2, e.g., obtainable from commercial tomato varieties Mobaci.

"Tm2 gene" or "Tm2 resistance gene" refers to the dominant resistance gene as known in the art, conferring resistance to ToMV strains 0 and 2, e.g., obtainable from commercial tomato varieties Moperon.

"$Tm2^2$ gene" or "$Tm2^2$ resistance gene" refers to the dominant resistance gene as known in the art, conferring resistance to ToMV strains 0, 1 and 2, e.g., obtainable from commercial tomato varieties Momor.

A plant (e.g. a Solanaceae, e.g. a wild relative of tomato or a cultivated tomato, a wild or cultivated *Capsicum* species, a aubergine or a pepino) having or comprising "ToMSV-resistance" or being "ToMSV-resistant" refers to a plant which does not develop systemic symptoms and in which the virus does, or does not, spread systemically (i.e. to non-inoculated and/or non-infected parts of the plant, such as upper leaves) after inoculation or infection with one or more infectious strains of ToMSV, such as strain V484. If the virus does not develop systemic symptoms and also cannot spread systemically, the resistance cane be called "complete resistance", while if the virus does not develop systemic symptoms but the virus can spread systemically, this resistance can also be called "tolerance" herein. Resistance (including complete resistance and tolerance) can be tested using various methods, one example is using an artificial mechanical inoculation assay, whereby, for example, the one or two young leaves or cotyledons of a plant are mechanically inoculated with an infectious strain (e.g. Ve484), and the non-inoculated plant parts (such as upper leaves) are evaluated one or more days post inoculation for systemic symptoms (such as mosaic, leaf distortion, blistering and/or bronzing) and/or for presence of the virus in non-inoculated plant parts (using e.g. ELISA, electron microscopy, etc.).

"Systemic symptoms" are symptoms that can be seen on other tissues or plant parts (e.g. other leaves) than the inoculated/infected tissue or plant part (e.g. true leaf or cotyledon or stem or hypocotyl), e.g. on upper leaves to which the virus has spread from the inoculated/infected leaf or cotyledon or stem or hypocotyl.

"Systemic spread" refers to the virus having spread from the inoculated/infected tissue or plant part (e.g. leaf or cotyledon or stem or hypocotyl) to non-inoculated/non-infected tissues or plant parts, e.g. to upper leaves.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species, such as pepper and tomato, may comprise a large number of different alleles at a particular locus. These may be identical alleles of the gene (homozygous) or two different alleles (heterozygous).

The term "protein" refers to a polypeptide having a mode of action, size, three-dimensional structure or origin. A "fragment" or "portion" of a protein may thus still be referred to as a "protein". An "isolated protein" is used to refer to a protein which is no longer in its natural environment.

"Sequence identity" and "sequence similarity" can be determined by alignment of two peptide or two nucleotide sequences using global or local alignment algorithms. Sequences may then be referred to as "substantially identical" or "essentially similar" when they (when optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimises the number of gaps. Generally, the default parameters are used, with a gap creation penalty=10 and gap extension penalty=0.5 (both for nucleotide and protein alignments). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may for example be determined using computer programs, such as the GCG Wisconsin Package, Version 10.3, available from Accelrys Inc., 9685 Scranton Road, San Diego, Calif. 92121-3752 USA or EMBOSS (http://www.ebi.ac.uk/Tools/webservices/services/emboss). Alternatively percent similarity or identity may be determined by searching against databases such as FASTA, BLAST, etc., but hits should be retrieved and aligned pairwise to compare sequence identity.

"Average" refers herein to the arithmetic mean.

"Stringent hybridisation conditions" can be used to identify nucleotide sequences (in method known as nucleic acid hybridization methods), which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) Molecular Cloning: A Laboratory Manual, Second Edition, Cold Spring Harbor Laboratory Press, and Sambrook and Russell (2001) Molecular Cloning: A Laboratory Manual, Third Edition, Cold Spring Harbor Laboratory Press, NY; and in Volumes 1 and 2 of Ausubel et al. (1994) Current Protocols in Molecular Biology, Current Protocols, USA.

DETAILED DESCRIPTION OF THE INVENTION

The present invention provides a new tobamovirus, referred herein to as Tomato Mosaic Severe Virus (ToMSV or TMSV), which was identified in a leaf sample from a tomato production field and was identified to be a tobamovirus by ELISA, electron microscopy and bioassays, and was found to be a new species of tobamovirus by sequencing of the viral genome. A strain of the virus was isolated and is referred to as strain VE484, which was deposited at the DSMZ. The strain VE484 is able to infect cultivated tomato plants comprising the widely used resistance genes Tm1, Tm2 and $Tm2^2$. It is also able to infect other Solanaceae, especially members of the genus *Capsicum*, such as cultivated pepper, and likely other members of the genus *Solanum*, besides *Solanum lycopersicum* (tomato), such as wild relatives of tomato, *Solanum melongena* (aubergine) and *Solanum muricatum* (pepino).

As in other tobamoviruses, the genome sequence (SEQ ID NO: 1 and SEQ ID NO: 2) of this positive sense single stranded RNA virus encodes four ORFs (Open Reading Frames). The entire genome is 6402 bases long and has only 82% sequence identity to the most similar virus, Genbank accession FR878069.1 (Tobacco Mosaic Virus Strain Ohio V, complete genome, genomic RNA). According to this low percentage (less than 90%) of genome sequence identity a new species designation within the genus tobamoviruses is therefore proposed, which is in accordance with the species demarcation criteria proposed in the book "Virus Taxonomy: $9^{th}$ report of the International Committee on Virus Taxonomy", ISBN 978-0-12-384684-6, p 1155. Herein viruses with nucleotide genome sequences with less than 90% sequence identity are proposed to be classified as a new genus.

Also the proteins encoded by the four ORFs are unique in public sequence databases. The percentage sequence identity to the most similar Genbank accessions is shown below, using Emboss-needle (pairwise alignments, default parameters):

TABLE 1

| ORF1 (SEQ ID NO: 3), protein p126 | | | |
|---|---|---|---|
| | ORF1 (SEQ ID NO: 3) | NP_078447.1 | AHW98774.1 |
| ORF1 (SEQ ID NO: 3) | 100% | | |
| NP_078447.1 | 92.7% | 100% | |
| AHW98774.1 | 92.7 | 99.7% | 100% |

The protein p126 (SEQ ID NO: 3) is 1116 amino acids in length, has a molecular weight of 126 kDa and contains a methyltransferase and a helicase domain.

TABLE 2

| ORF2 (SEQ ID NO: 4), protein p183 | | | |
|---|---|---|---|
| | ORF2 (SEQ ID NO: 4) | CCC33060.1 | ABN79257.1 |
| ORF2 (SEQ ID NO: 4) | 100% | | |
| CCC33060.1 | 93.0% | 100% | |
| ABN79257.1 | 92.9% | 98.8% | 100% |

The protein p183 (SEQ ID NO: 4) is 1609 amino acids in length and has a molecular weight of 183 kDa and contains a methyltransferase and a helicase domain (as does p126) and additionally a polymerase domain (RdRP). Protein p183 results from suppression of the p126 stop codon.

TABLE 3

| ORF3 (SEQ ID NO: 5), Movement Protein | | | |
|---|---|---|---|
| | ORF3 (SEQ ID NO: 5) | AAY44881.1 | CCC33061.1 |
| ORF3 (SEQ ID NO: 5) | 100% | | |
| AAY44881.1 | 79.4% | 100% | |
| CCC33061.1 | 79.4% | 96.3% | 100% |

The protein of SEQ ID NO: 5 (ORF3) is 266 amino acids in length, has a molecular weight of 29.7 kDa, and is the viral movement protein (MP).

TABLE 4

| ORF4 (SEQ ID NO: 6), Coat Protein | | | |
|---|---|---|---|
| | ORF4 (SEQ ID NO: 6) | AIW42686.1 | ABN13962.1 |
| ORF4 (SEQ ID NO: 6) | 100% | | |
| ABN13962.1 | 81.8 | 100% | |
| AIW42686.1 | 80.7 | 96.9 | 100% |

The protein of SEQ ID NO: 6 (ORF4) is 176 amino acids in length, has a molecular weight of 19.6 kDa, and is the viral Coat Protein (CP).

The virus is not insect-vector transmitted, but is mechanical transmitted. It might also be transmitted via seeds (i.e. seeds produced on infected plants) as the virus was found to be seed born.

Electron microscopy of infected leaves showed that virus particles are rod-shaped, with about 300 nanometer (nm) length and 18 nm diameter. The virus can be propagated on Solanaceae, e.g. *S. lycopersicum* or *Nicotiana benthamiana*, using mechanical inoculation of leaves.

In one aspect the invention provides a new species of tobamovirus whose genome sequence comprises substantial sequence identity to SEQ ID NO: 1, i.e. at least 83% sequence identity to SEQ ID NO:1, preferably at least 84%, 85%, 86%, 87%, 88%, 89%, 90%, 91%, 92%, 93%, 94%, 95%, 96%, 97%, 98% or even 99% or 100%. In one aspect the invention provides a new species of tobamovirus whose nucleic acid genome sequence comprises substantial sequence identity to SEQ ID NO: 1, wherein substantial sequence identity means at least 90%, preferably at least 91%, 92%, 93% or more (e.g. at least 94%, 95%, 96%, 97%, 98% or even 99% or 100%) sequence identity to SEQ ID NO: 1 (also shown in FIG. 1). The sequence identity is determined by using a pairwise alignment of the entire genome sequences, using e.g. the Emboss program 'Needle' (using default parameters). Apart from strain VE484 (a representative sample of which has been deposited), other strains of this new species exist or will develop. The skilled person can easily isolate and identify such other strains based on the instant invention, such as one or more criteria selected from sequence identity, bioassays, symptoms, antibody based assays, etc.

In one aspect the tobamovirus is provided whereby it is not present in a living plant (i.e. the virus is isolated from a whole living plant such as a plant found in the field), but is provided in e.g. a severed plant part such as fresh leaf tissue, freeze dried plant tissue, or in extracted plant sap or in a solution such as a buffer. It is also provided in a container comprising the virus.

The virus is infectious on Solanaceae species, especially on species of the genus *Solanum* and *Capsicum*. In one aspect the virus causes systemic symptoms on species of the genus *Solanum*, such as at least on *Solanum lycopersicum*, especially cultivated *S. lycopersicum* lacking Tm resistance genes or comprising one or more Tm resistance genes selected from Tm1, Tm2 and $Tm2^2$. The virus for example causes systemic symptoms on tomato cultivars having the following genotypes: Tm1/Tm1 (homozygous for Tm1); Tm1Tm2/Tm1Tm2 (homozygous for Tm1 and Tm2); Tm1/$Tm2^2$/Tm1/$Tm2^2$ (homozygous for Tm1 and $Tm2^2$); Tm2/Tm2 (homozygous for Tm1); $Tm2^2$/$Tm2^2$ (homozygous for $Tm2^2$).

In a further aspect the virus causes systemic symptoms on plants of the genus *Capsicum*, especially on cultivated pepper of the species *C. annuum*.

Systemic symptoms are symptoms in other parts of plant than where the virus entered or was inoculated. This means the virus is able to spread from an infection site (e.g. a leaf) to other parts of the plant, e.g. other leaves, such as upper leaves (i.e. the virus spreads systemically). The systemic symptoms vary, and include one or more of: mosaic, leaf distortion, leaf blistering and/or leaf bronzing. In some instances plants also remain asymptomatic, even though the virus has spread systemically. Therefore, in one aspect the ability of the virus to cause systemic symptoms means that in at least 40%, 50%, 60%, preferably in at least 70%, 80%, 85%, 90% or more of plants of the same genotype which are infected by the virus (e.g. in the field or via seed transmission) or inoculated (e.g. mechanically inoculated) one or more systemic symptoms develop. Such a plant genotype is thus susceptible to the virus, even though not all plants show systemic symptoms.

In both symptomatic and in asymptomatic plants the systemic spread of the virus can be determined by various methods, which detect (and optionally quantify) the presence of the virus in non-infected or non-inoculated parts of the plant, such as in upper leaves. The virus can be detected by various methods or combinations thereof, including microscopy (e.g. Electron Microscopy), antibody based tests such as ELISA or Lateral Flow Device tests, RT-PCT (reverse transcriptase PCR), sequencing, nucleic acid hybridization methods (using e.g. stringent hybridization conditions), bioassays, e.g. inoculation of indicator plants such as *Nicotiana tabacum* var. *Xanthi* (comprising the N gene in homozygous form) and *Nicotiana glutinosa*, etc.

In a further aspect a container comprising the new species of tobamovirus is provided. Preferably the container comprises one strain of the virus, preferably an infectious strain. A container may be any container, such as a tube, a vial, a well, a bottle, bag, etc. The virus may be present in the container in various forms, such as in severed plant tissue (e.g. a fresh, dried or lyophilized tissue, such as leaf or leaf part, stem or stem part, seed or seed part, etc.). The virus may also be present outside of plant tissue, e.g. in a liquid, such as extracted plant sap, or in a solution not comprising plant cells and not comprising plant sap, such as water, or a buffer solution.

In one aspect a sterilized solution comprising the virus according to the invention is provided. In one aspect the virus is a single infectious strain, such as VE484 or any other ToMSV strain. In one aspect the solution is a buffer solution.

Also provided is a method of using the virus according to the invention for identifying plants of the genus *Solanum* or of the genus *Capsicum* which comprise resistance against the virus, either complete resistance or tolerance. The new virus can be used to screen different plant genotypes of the genus *Solanum* and/or *Capsicum* for plant genotypes which are resistant (completely resistant or tolerant). In one aspect this means that the virus does not cause systemic symptoms and does not spread systemically (complete resistance) on a plant genotype. The virus may optionally cause local lesions on inoculated plant parts (e.g. leaves) of the genotype. In another aspect the virus does not cause systemic symptoms but does spread systemically (tolerance) on a plant genotype.

The methods can be used to identify a cultivated plant (e.g. cultivated tomato, *S. lycopersicum*, or cultivated pepper, *Capsicum annuum*) or preferably a wild plant of the genus *Solanum* or *Capsicum* comprising ToMSV resistance. Thus, in one aspect the method is used to identify a ToMSV resistant plant (e.g. a VE484 resistant plant) wherein the plant is selected from the species *S. lycopersicum, S. arcanum, S. chmielewskii, S. neorickii* (=*L. parviflorum*), *S. cheesmaniae, S. galapagense, S. pimpinellifolium, S. chilense, S. comeliomulleri, S. habrochaites* (=*L. hirsutum*), *S. huaylasense, S. sisymbriifolium, S. peruvianum, S. hirsutum, S. pennellii, S. lycopersicoides, S. sitiens* or *S. ochranthum.*

In another aspect the method is used to identify a ToMSV resistant plant (e.g. a VE484 resistant plant) wherein the plant is selected from the species *Capsicum annuum* L., *Capsicum chinense* Jacq., *Capsicum frutescens* L., *Capsicum baccatum* L., and *Capsicum pubescens.*

In yet another aspect the method is used to identify a ToMSV resistant plant (e.g. a VE484 resistant plant) wherein the plant is selected from the species *Solanum melongena* or *Solanum muricatum.*

The method comprises the steps of:

a) providing one or more plants;

b) providing inoculum comprising the virus according to the invention;

c) inoculating one or more plant parts of the plants of a) with the inoculum of b);

d) incubating the inoculated plants.

Thus, as mentioned, the one or more plants of step a) are preferably one or more plants of the genus *Solanum* or *Capsicum*, such as one or more plants of the species mentioned above. When reference to "one or more plants" is made it is understood that preferably several plants of one or more plant genotypes is referred to. So for example if one or more genotypes (or accessions) are tested, such as one or more wild accessions of relatives of tomato, preferably several plants of each genotype are provided, e.g. at least 2, 3, 4, 5, 6, 7, 8, 9, 10, 11, 12, 13, 14, 15 or more plants of each genotype. Similarly if one or more breeding lines or cultivars are to be tested, several plants of each breeding line or cultivar are provided. Preferably also a ToMSV susceptible plant genotype with known symptomatology is included, such as tomato variety Mobaci, Moperou, Momor, Mocimor, Philippos or others.

An inoculum of the virus can be made using known methods. E.g. symptomatic leaves or other infected plant tissue can be collected and ground in the presence of a buffer or infectious plant sap can be used. The virus as deposited can also be used to make infectious inoculum. It is noted that the skilled person does not need to use the virus strain as deposited (VE484, DSM29970), but can identify a strain of the new tobamovirus in the field, optionally verifying the identity by sequencing the virus strain, and can use the strain to make infectious inoculum.

Step c) is preferably carried out by mechanical inoculation, i.e. the plant surface is mechanically damaged slightly to allow the virus to enter. So, for example one or more leaves or cotyledons of each plant may be dusted with e.g. carborundum powder before the inoculum is added to the leaf surface or cotyledon. Alternatively, other plant parts may be inoculated, such as a part of the stem, the hypocotyl, the petiole or the root. It is clear that there are different ways to slightly damage the plant surface. Thus, in one aspect the plant part of c) is a leaf, a cotyledon, a stem, a hypocotyl, a root or a petiole.

In step d) the plants are then incubated at a temperature, light and relative humidity which allows the plants to grow further (depending on the species). The plants may then be inspected regularly for systemic symptoms and/or for local lesions, e.g. after at least 1, 2, 3, 4, 5, 6, 7, 8, 9, 10, 11, 12, 13, 14, 15, 16, 17, 18 and/or more days post-inoculation.

Thus, in one aspect the method further comprises step e): assessing symptoms on the plants or plant parts, especially systemic symptoms and/or local lesions (on the inoculated plant part). "Local lesions" or "local necrotic lesions" are lesions which form as a defence reaction of the plant and which prevent the spread of the virus to non-inoculated parts. Thus systemic virus symptoms such as one or more of mosaic, leaf distortion, blistering and/or bronzing may be assessed, especially on non-inoculated parts of the plant, such as upper leaves. Symptom assessment can be made visually. Optionally the method further comprises step f) determining (or assessing) the presence of the virus particles in non-inoculated plant parts, such as upper true leaves. This can be done on one or more or all of the inoculated plants. In one aspect it is carried out on one or more plants which show no systemic symptoms.

In one aspect step e) above is omitted, i.e. symptoms are not assessed but the presence of virus particles in (one or more) non-inoculated plant parts is assessed one or more of the inoculated plants.

Following step e) or f) one can identify (make a selection of) a resistant or of a tolerant plant, or alternatively discard all susceptible plants. The identification can be made in various ways:

In one aspect the method further comprises identifying a plant (or a number of plants) which has no systemic symptoms and in which the virus particles are not present in non-inoculated plant parts. Such plants can be considered resistant against the virus.

In another aspect the method further comprises identifying a plant (or a number of plants) which has local lesions on the inoculated plant part and/or in which the virus particles are not present in non-inoculated plant parts. Such plants can be considered resistant against the virus.

In yet another aspect the method further comprising identifying a plant which has no systemic symptoms and in which the virus particles are present in non-inoculated parts of the plant. Such a plant can be considered tolerant against the virus, i.e. even though the virus is capable of spreading systemically, it does not cause systemic symptoms.

In still another aspect the method further comprising identifying a plant which has significantly reduced systemic symptoms compared to susceptible control plants and in which the virus particles are present in non-inoculated parts of the plant. Such a plant can be considered as being partially resistant against the virus. Significantly reduced systemic symptoms may for example be that the percentage of plant of the genotype showing one or more systemic symptoms is statistically significantly lower than the percentage of susceptible control plants showing one or more systemic symptoms. So, for example if 100% of plants of the susceptible control genotype show one or more systemic symptoms, in a partially resistant genotype significantly less plants show one or more systemic symptoms, such as less than 90%, 80%, 70%, 60%, 50% or even less than 40% of the inoculated plants show one or more systemic symptoms.

The presence of virus particles in non-inoculated plant parts can be determined in various ways and can optionally be quantified. So, for example an ELISA test as described in the Examples can be carried out on non-inoculated parts, e.g. upper leaves of the plants in order to determine whether the virus is present and has thus spread systemically. Different methods can be used to detect the virus, such as microscopy (e.g. Electron Microscopy), antibody based assays (e.g. ELISA or Lateral Flow Device Tests), or tests which detect virus RNA (or cDNA), such as Polymerase Chain Reaction (PCR) based methods, nucleic acid sequence, nucleic acid hybridization methods, or bioassays e.g. inoculation of indicator plants such as *Nicotiana tabacum* var. *Xanthi* (comprising the N gene in homozygous form) and *Nicotiana glutinosa*, etc.

Optionally plants which do not contain the virus in non-inoculated plant parts may be selected and/or plants do contain the virus in non-inoculated plant parts may be discarded. Thus in one aspect the method comprises determining the presence of virus particles in non-inoculated plant parts.

The identified plant (or plant genotype) may also be re-tested in the above method(s), i.e. one or more identified plants may be inoculated again with the virus and incubated again, to confirm their resistance or partial resistance against the ToMSV strain in a second assay or third assay. Also different ToMSV strains may be tested. As in the initial screen it may have been that only a few plants of a genotype are tested (e.g. 1, 2, 3, 4 plants) and as only 1 or a few plants of a genotype may be identified and selected in the initial screen, it is preferred that in a second or third screen a larger number of plants of the identified genotype are re-tested, such as at least 10, 11, 12, 13, 14, 15, 16, 17, 18, 19, 20, 21, 22, 23, 34, 25, 26, 27, 28, 29, 30 or more.

When a larger number of plants of a given genotype are tested in any of the above methods, preferably at least 80%, 90%, 91%, 92%, 93%, 94%, 95%, 97%, 98%, 99% or most preferably 100% of plants of the same genotype are identified as being completely resistant. Likewise in one aspect preferably at least 80%, 90%, 91%, 92%, 93%, 94%, 95%, 97%, 98%, 99% or most preferably 100% of plants of the same genotype are identified as being tolerant.

The above methods can, therefore, be used to identify plants, especially wild relatives of tomato or wild accessions of *Capsicum*, or plants of aubergine or pepino, comprising resistance against one or more strains of ToMSV, e.g. against VE484. Plants obtained by the above method are encompassed herein. The resistance genes found in such plants can then be used to make cultivated tomato plants or cultivated pepper plants or cultivated aubergine or pepino comprising resistance against one or more strains of ToMSV, e.g. against at least against strain VE484. Such plants can be made by traditional breeding techniques.

In a further aspect the invention provides a method for assessing the presence of a virus according to the invention in a plant or plant part, said method comprising the steps of:

a) determining the presence of a nucleic acid molecule comprising at least 83% sequence identity to SEQ ID NO:1 in the plant or plant part; and/or
b) determining the presence of a protein, or of a nucleic acid molecule encoding a protein, comprising at least 93% sequence identity to SEQ ID NO: 3; and/or
c) determining the presence of a protein, or of a nucleic acid molecule encoding a protein, comprising at least 94% sequence identity to SEQ ID NO: 4; and/or
d) determining the presence of a protein, or of a nucleic acid molecule encoding a protein, comprising at least 80% sequence identity to SEQ ID NO: 5; and/or
e) determining the presence of a protein, or of a nucleic acid molecule encoding a protein, comprising at least 82% sequence identity to SEQ ID NO: 6.

As the virus is an RNA virus, the nucleic acid molecule is an RNA molecule. RNA molecules are generally detected by first reverse transcribing the RNA into DNA (complementary DNA or cDNA) and then detecting the cDNA. RNA and cDNA have the same nucleotide base sequence, except that Uracil (U) of RNA is replaced by Thymine (T). Therefore detection of the cDNA is equivalent to detection of the RNA molecule.

The presence of a nucleic acid molecule according to any of steps a), b), c), d) or e) can be easily determined by the skilled person using known methods. For example, the skilled person can design a pair of primers for RT-PCR and carry out an RT-PCR assay to amplify the nucleic acid molecule or part thereof. Also nucleic acid hybridization methods may be used (using e.g. stringent conditions).

Regarding step a) the primers can be designed to amplify any part of SEQ ID NO: 1 (the nucleic acid sequence of the genome of VE484) or of a nucleic acid molecule comprising at least 83% sequence identity to SEQ ID NO:1, e.g. at least 84%, 85%, 86%, 87%, 88%, 89%, 90%, 91%, 92%, 93%, 94%, 95%, 96% or 97%, 98% or 99% sequence identity to SEQ ID NO: 1. Optionally the primers of primer pair SEQ ID NO: 7 and 8 or SEQ ID NO: 9 and 10 can be used.

For detection of a nucleic acid sequence encoding a comprising at least 93% (e.g. at least 94%, 95%, 96%, 97%, 98%, 99% or 100%) sequence identity to SEQ ID NO: 3; and/or comprising at least 94% (e.g. at least 95%, 96%, 97%, 98%, 99% or 100%) sequence identity to SEQ ID NO: 4; and/or comprising at least 80% (e.g. at least 81%, 82%, 83%, 84%, 85%, 86%, 87%, 88%, 89% 90%, 91%, 92%, 93%, 94%, 95%, 96%, 97%, 98%, 99% or 100%) sequence identity to SEQ ID NO: 5; and/or comprising at least 82% (e.g. at least 83%, 84%, 85%, 86%, 87%, 88%, 89% 90%, 91%, 92%, 93%, 94%, 95%, 96%, 97%, 98%, 99% or 100%) sequence identity to SEQ ID NO: 6, various methods can be used, such as also the design of primer pairs (or degenerate primer pairs) which amplify such nucleotide sequences and detect the presence of an RNA molecule having that sequence in a sample. Again RT-PCR can for example be used. Also nucleic acid hybridization methods may be used (using e.g. stringent conditions).

The nucleotide sequences encoding the protein of SEQ ID NO: 3, 4, 5 and 6 are shown in SEQ ID NO: 1 and 2. The protein of SEQ ID NO: 3 is encoded by nucleotides 77 to 3424 of SEQ ID NO: 1. The protein of SEQ ID NO: 4 is encoded by nucleotides 77 to 3424 and by 3446 to 4921 of SEQ ID NO:1. The protein of SEQ ID NO: 5 is encoded by nucleotides 4911 to 5708 of SEQ ID NO: 1 and the protein of SEQ ID NO: 6 is encoded by nucleotides 5671 to 6198 of SEQ ID NO: 1.

Regarding the determination of the presence of a protein comprising at least 93% (e.g. at least 94%, 95%, 96%, 97%, 98%, 99% or 100%) sequence identity to SEQ ID NO: 3; and/or comprising at least 94% (e.g. at least 95%, 96%, 97%, 98%, 99% or 100%) sequence identity to SEQ ID NO: 4; and/or comprising at least 80% (e.g. at least 81%, 82%, 83%, 84%, 85%, 86%, 87%, 88%, 89% 90%, 91%, 92%, 93%, 94%, 95%, 96%, 97%, 98%, 99% or 100%) sequence identity to SEQ ID NO: 5; and/or comprising at least 82% (e.g. at least 83%, 84%, 85%, 86%, 87%, 88%, 89% 90%, 91%, 92%, 93%, 94%, 95%, 96%, 97%, 98%, 99% or 100%) sequence identity to SEQ ID NO: 6, various methods can be used. In one aspect preferably antibody based methods are used, such as ELISA or LFD. One can use any capture antibody which can bind one of the above proteins (to form an antibody-antigen complex). The proteins or protein parts may be used as antigens i.e. to raise and make antibodies which bind the proteins. The examples also show that the TMV antibody sold by Agdia, Inc. (Catalog numbers CAB57400, ECA 57400, PSA 57400 and SRA57400), can be used to detect the strain VE484.

In another aspect an isolated nucleic acid molecule comprising at least 83% (e.g. at least 84%, 85%, 86%, 87%, 88%, 89% 90%, 91%, 92%, 93%, 94%, 95%, 96%, 97%, 98%, 99% or 100%) sequence identity to SEQ ID NO: 1, or a part thereof, is provided. The nucleic acid molecule may be a RNA or DNA molecule. A part thereof may be a fragment, such as any molecule comprising at least 15, 20, 30, 40, 50, 100, 200, 500, 1000, 1500, 2000, 2500, 3000, 3500, 4000, 4500, or 6000 consecutive nucleotides of such a nucleic acid molecule.

In still a different aspect an isolated nucleic acid molecule comprising at least 80% (e.g. at least 81%, 82%, 83%, 84%, 85%, 86%, 87%, 88%, 89% 90%, 91%, 92%, 93%, 94%, 95%, 96%, 97%, 98%, 99% or 100%) to nucleotides 77 to 3424 of SEQ ID NO: 1 is provided.

In still a different aspect an isolated nucleic acid molecule comprising at least 80% (e.g. at least 81%, 82%, 83%, 84%, 85%, 86%, 87%, 88%, 89% 90%, 91%, 92%, 93%, 94%, 95%, 96%, 97%, 98%, 99% or 100%) to nucleotides 3446 to 4921 of SEQ ID NO: 1 is provided.

In still a different aspect an isolated nucleic acid molecule comprising at least 80% (e.g. at least 81%, 82%, 83%, 84%, 85%, 86%, 87%, 88%, 89% 90%, 91%, 92%, 93%, 94%, 95%, 96%, 97%, 98%, 99% or 100%) to nucleotides 4911 to 5708 of SEQ ID NO: 1 is provided.

In still a different aspect an isolated nucleic acid molecule comprising at least 80% (e.g. at least 81%, 82%, 83%, 84%, 85%, 86%, 87%, 88%, 89% 90%, 91%, 92%, 93%, 94%, 95%, 96%, 97%, 98%, 99% or 100%) to nucleotides 5671 to 6198 of SEQ ID NO: 1.

Also provided is a protein selected from the group consisting of: a protein comprising at least 93% (e.g. at least 94%, 95%, 96%, 97%, 98%, 99% or 100%) sequence identity to SEQ ID NO: 3, a protein comprising at least 94% (e.g. at least 95%, 96%, 97%, 98%, 99% or 100%) sequence identity to SEQ ID NO: 4, a protein, comprising at least 80% (e.g. at least 81%, 82%, 83%, 84%, 85%, 86%, 87%, 88%, 89% 90%, 91%, 92%, 93%, 94%, 95%, 96%, 97%, 98%, 99% or 100%) sequence identity to SEQ ID NO: 5 and a protein comprising at least 82% (e.g. at least 83%, 84%, 85%, 86%, 87%, 88%, 89% 90%, 91%, 92%, 93%, 94%, 95%, 96%, 97%, 98%, 99% or 100%) sequence identity to SEQ ID NO: 6.

Another aspect of the invention is an antibody raised against a protein or protein part selected from the group consisting of: a protein comprising at least 93% (e.g. at least 94%, 95%, 96%, 97%, 98%, 99% or 100%) sequence identity to SEQ ID NO: 3, a protein comprising at least 94% (e.g. at least 95%, 96%, 97%, 98%, 99% or 100%) sequence identity to SEQ ID NO: 4, a protein, comprising at least 80% (e.g. at least 81%, 82%, 83%, 84%, 85%, 86%, 87%, 88%, 89% 90%, 91%, 92%, 93%, 94%, 95%, 96%, 97%, 98%, 99% or 100%) sequence identity to SEQ ID NO: 5 and a protein comprising at least 82% (e.g. at least 83%, 84%, 85%, 86%, 87%, 88%, 89% 90%, 91%, 92%, 93%, 94%, 95%, 96%, 97%, 98%, 99% or 100%) sequence identity to SEQ ID NO: 6. Such an antibody can be used to detect ToMSV strains in plant tissues or in extracts of plant tissues. A kit comprising such an antibody is a further aspect of the invention. Such a kit may e.g. be an ELISA kit or a LFD kit.

Also use of the virus of the invention for identifying resistant plants or partially resistant plants of the genus *Solanum* or *Capsicum* is provided herein.

Likewise use of the nucleic acid molecules (or sequences), protein molecules (or sequences), or parts of any of these, for detection of the virus of the invention in a plant, plant part or in a sample is provided.

DEPOSIT INFORMATION

A representative sample of the the ToMSV strain Ve484 was deposited by Nunhems B.V. at the DSMZ (Deutsche Sammlung von Mikroorganismen und Zellkulturen GmbH, Inhoffenstrasse 7 B, 38124 Braunschweig, Germany) on Jan. 19, 2015, under accession number DSM 29970.

The Applicant requests that samples of the biological material and any material derived therefrom be only released to a designated Expert in accordance with Rule 32(1) EPC or related legislation of countries or treaties having similar rules and regulation, until the mention of the grant of the patent, or for 20 years from the date of filing if the application is refused, withdrawn or deemed to be withdrawn.

Access to the deposit will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The following non-limiting examples illustrate the production of pepper plants, seeds and fruits according to the invention. All references mentioned herein are incorporated by reference.

EXAMPLES

Example 1—Identification of ToMSV

Tomato plants with mosaic symptoms were identified in a leaf sample from a tomato production field. The tomato plants carried the $Tm2^2$ resistance gene in homozygous form.

1.1 Lateral Flow Device Test

Symptomatic leaves were collected and a Lateral Flow Device Test was carried out using an ImmunoStrip® test (ISK 57400/0025) for TMV (Tobacco Mosaic Virus) detected provided by Agdia, Inc. using the manufacturer's instructions. In short: Symptomatic leaf tissue is placed in an extraction bag (between mesh lining) containing SEB1 buffer. The virus is extracted by rubbing the bag between the mesh lining. Then the immunostrip is placed into the so-called channel portion of the bag for 30 minutes. A control line will become visible if the test was performed adequately. If virus is present also a pink/purple test line will appear on the strip. The antibody in the test detects a number of viruses (but not all) from the tobamovirus group.

The test was positive, indicating that the mosaic symptoms are caused by a member of the tobamovirus group.

1.2 Detection of the Virus in Tomato Seeds

Seeds were collected from infected plants found in the production field.

Two assays were carried out using the seeds, an ELISA assay (Agdia, Inc.) followed by a local lesion assay on *Nicotiana tabacum* plants as described in the ISF protocol "Method for the detection of infectious tobamoviruses on tomato seed" (found on the world wide web at worldseed-.org/cms/medias/file/TradeIssues/PhytosanitaryMatters/SeedHealthTesting/ISHI-Veg/Tomato_Tobamo_Sept_2013.pdf).

1.2.1 Sample Preparation

Twelve inoculum samples were prepared from 250 tomato seeds each, by grinding the seed samples in extraction buffer. Also seeds from positive and negative controls samples were made. The inoculum samples were used first in the ELISA and then in the local lesion assay.

1.2.1 ELISA

The ELISA assay was carried out using the Tobacco Mosaic Virus ELISA Complete Kit (PSA 57400/0288) of Agdia, Inc. according to manufacturer's instructions. In short, this test uses a 96-well microtitre plate coated with an antibody that detects detects a number of viruses (but not all) from the tobamovirus group. Tissue samples (e.g. leaf tissue, seeds, etc.) are ground in extraction buffer and diluted. The samples are then loaded into the microtriter wells, together with the provided controls (positive control, negative control and buffer only) and incubated. After incubation the plates are washed and freshly prepared alkaline phosphatase enzyme conjugate is dispensed into the wells, which are then incubated again. The plates are washed again and PNP substrate is added to each well, which are then incubated again. The results are examined by eye and/or using a plate reader at 405 nm. Colored wells are positive for virus when examined by eye and/or a 405 nm reading of 2.5 times the background (negative control) is positive for the virus. Test results are only valid if the positive control is colored and the negative control is virtually clear and buffer-only wells are colorless.

1.2.2 the Local Lesion Assay

The local lesion assay is a bioassay which is used to detect infectious virus particles by mechanically inoculating leaves of *Nicotiana tabacum* var. *Xanthi* and *Nicotiana glutinosa*, both carrying the N gene for resistance against TMV. 3000 tomato seeds were used in the assay.

The *Nicotiana* plants were grown to the 4-5 true leaf stage and two leaves per plant were dusted with carborundum powder and inoculated with one of the 12 inoculum samples or with a control inoculum sample. Inoculation was done by rubbing a sponge with inoculum on the carborundum dusted leaf and smearing the entire surface of the leaf with the sponge. After inoculation the plants were incubated for 5-7 days at 20-25 degrees Celsius with at least 12 hours light and then the number of necrotic lesions on the inoculated leaves was recorded.

Such local necrotic lesions (hypersensitive response) show that one or more seeds of the 250 seed sample contained infectious virus particles.

Results

The Tomato Mosaic Severe Virus strain was detected in tomato seeds of infected plants both in the ELISA assay and in the local lesion assay. The strain is therefore seed borne.

1.3 Sequencing and Sequence Analysis

Seed-extract inoculated tobacco leaves were used to prepare inoculum for mechanical inoculation of *N. benthamiana* leaves. The leaves were mechanically inoculated (using carborundum as described above) and the presence of virus particles in the inoculated leaves were confirmed by Electron Microscopy. RNA was isolated using the following primer combinations for RT-PCR (reverse transcriptase PCR) and sequencing:

```
                                        (SEQ ID NO: 7)
Tob-Uni 1   5'-ATTTAAgTggASggAAAAVCACT-3'

                                        (SEQ ID NO: 8)
Tob-Uni 2   5'-GTYGTTGATGAGTTCRTGGA-3'
or

                                        (SEQ ID NO: 9)
Tobamo F    5'-GWCGCSGAKTCKGATTCGTWTTAAATATG-3'

                                       (SEQ ID NO: 10)
Tobamo R    5'-TGGGCCSCTACCSGSGG-3'
```

Several different samples were sequenced and sequences were compared.

The genomic virus sequence is provided in SEQ ID NO: 1 and SEQ ID NO: 2 and in FIG. 1.

In SEQ ID NO: 1 ORF1 and ORF3 are shown, while in SEQ ID NO: 2 ORF2 (only final 492 amino acids are shown) and ORF4 are shown.

BLAST (Basic Local Alignment Search Tool) was carried out on the NCBI website using default parameters and also pairwise alignments using the program Needle were done with the best BLAST hits (using EMBOSS—needles, default parameters).

The BLAST result and pairwise alignment of the genome sequence of SEQ ID NO: 1 showed that the most similar virus in the database has only 82% sequence identity to the present virus, indicating that the present virus is a new species of tobamovirus. The most similar virus is Genbank accession FR878069.1 (Tobacco Mosaic Virus Strain Ohio V, complete genome, genomic RNA). See the world wide web at ncbi.nlm.nih.gov/nuccore/FR878069.1. The virus is also different from the recently sequenced ToMMV (Tomato Mottle Mosaic Virus) found in Mexico, USA and China (Genbank accession KF477193) with which it shares only 80.8% sequence identity.

Four ORFs were present in the genome. ORF1 encodes protein p126, provided in SEQ ID NO: 3. ORF2 encodes protein p183, provided in SEQ ID NO: 4. The protein of SEQ ID NO: 4 results from suppression of the stop codon at the end of ORF1. ORF3 encodes the movement protein, provided in SEQ ID NO: 5. ORF4 encodes the Coat Protein, provided in SEQ ID NO: 6.

The new species of tobamovirus is named herein Tomato Mosaic Severe Virus (ToMSV or TMSV) and the infectious strain sequenced and deposited is named VE484.

Example 2—Bioassays of the New ToMSV Virus on Tomato and Pepper (Results not Shown)

Differential genotypes of tomato varieties comprising different TMV/ToMV resistance genes were inoculated mechanically with the deposited virus strain, VE484. The genotypes were inoculated in the biological assay were:

| Tomato variety | Genotype |
|---|---|
| Mobaci | Tm1/Tm1 (homozygous for Tm1) |
| Moperou | Tm2/Tm2 (homozygous for Tm2) |
| Momor | $Tm2^2/Tm2^2$ (homozygous for $Tm2^2$) |
| Mocimor | $Tm2^2$ Tm1/$Tm2^2$ Tm1 (homozygous for Tm1 and for $Tm2^2$) |
| Philippos | $Tm2^2/Tm2^2$ (homozygous for $Tm2^2$) |

All the plants were inoculated at 15 days stage and evaluated visually at 15 days post inoculation, when systemic symptoms were recorded. 12 plants per genotypes were inoculated.

These different genotypes showed a range of systemic symptoms: leaf mosaic, leaf distortion, blistering and bronzing. A LFD test was used to confirm the presence of the virus in the symptomatic leaves.

All plants showed symptoms and were therefore susceptible to the virus. The virus can therefore cause systemic symptoms on plants homozygous for Tm1 and/or Tm2 or $Tm2^2$ resistance genes.

| Tomato variety | Genotype | No. of plants | No of plants with mosaic symptoms | No of plants with leaf distortion | No of plants with leaf blistering | No of plants with leaf bronzing | Lateral Flow Device Test |
|---|---|---|---|---|---|---|---|
| Mobaci | Tm1/Tm1 | 12 | 3 | 5 | 4 | 0 | positive |
| Moperou | Tm2/Tm2 | 12 | 3 | 4 | 1 | 0 | positive |
| Momor | $Tm2^2/Tm2^2$ | 12 | 8 | 2 | 5 | 10 | positive |
| Mocimor | $Tm2^2$ Tm1/ $Tm2^2$ Tm1 | 12 | 4 | 3 | 3 | 0 | positive |
| Philippos | $Tm2^2/Tm2^2$ | 12 | 11 | 1 | 3 | 0 | positive |

The results were further confirmed in an ELISA test, where as a negative control a healthy, non-infect tomato variety was included and also, as positive control, the susceptible variety Monalbo was included (lacking Tm resistance genes) (data not shown). The results of the ELISA also confirmed that the new ToMSV virus strain VE484 can overcome all the known tobamovirus resistance genes, Tm1 (also referred to as Tm-1), Tm2 (also referred to as Tm-2) and $Tm2^2$ (also referred to as Tm-22).

The invention claimed is:

1. A method for identifying one or more plants comprising resistance against a tobamovirus whose genome comprises at least 95% sequence identity to SEQ ID NO: 1, comprising inoculating one or more plant parts of the genus *Solanum* with an inoculum comprising an infectious dose of the tobamovirus;

incubating the inoculated plants; and identifying one or more plants that do not develop systemic symptoms or plants that have reduced systemic symptoms after inoculation with the tobamovirus when compared to a susceptible control plant, thereby identifying one or more plants comprising resistance to the tobamovirus, wherein the virus causes systemic symptoms on *Solanum lycopersicum* plants homozygous for one or more Tm resistance genes of Tm1, Tm2, and/or $Tm2^2$.

2. The method according to claim 1, wherein identifying further comprises assessing symptoms on the plants or plant parts.

3. The method according to claim 1, wherein identifying further comprises determining the presence of virus particles in non-inoculated plant parts.

4. The method of claim 1, wherein the one or more plants comprising resistance to the tobamovirus have no systemic symptoms and in which the virus particles are not present in non-inoculated parts of the plant.

5. The method of claim 1, wherein the one or more plants comprising resistance to the tobamovirus have local lesions on the inoculated plant part and/or in which the virus particles are not present in non-inoculated parts of the plant.

6. The method of claim 1, wherein the one or more plants comprising resistance to the tobamovirus have no systemic symptoms and in which the virus particles are present in non-inoculated parts of the plant.

7. The method according to claim 1, wherein the plant part is a leaf, a cotyledon, a hypocotyl, a stem, a petiole or a root.

8. The method according to claim 1, wherein the plant is *Solanum lycopersicum, Solanum melongena, Solanum muricatum, Solanum arcanum, Solanum chmielewskii, Solanum neorickii, Solanum cheesmaniae, Solanum galapagense, Solanum pimpinellifolium, Solanum chilense, Solanum corneliomulleri, Solanum habrochaites, Solanum huaylasense, Solanum sisymbriifolium, Solanum peruvianum, Solanum hirsutum, Solanum pennellii, Solanum lycopersicoides, Solanum sitiens*, or *Solanum ochranthum.*

9. The method according to claim 1, wherein identifying further comprises assessing symptoms on the plants or plant parts and determining the presence of virus particles in non-inoculated plant parts.

10. The method according to claim 3, wherein the presence of virus particles is determined using microscopy, an antibody based assay, or a test that detects RNA or cDNA.

11. The method according to claim 10, wherein the microscopy is electron microscopy.

12. The method according to claim 10, wherein the antibody based test is an ELISA or lateral flow device test.

13. The method according to claim 10, wherein the test that detects virus RNA or cDNA is a Polymerase Chain Reaction (PCR) based method, a nucleic acid hybridization method, or a bioassay.

14. The method of claim 1, wherein the virus causes systemic symptoms on *Solanum lycopersicum* plants homozygous for $Tm2^2$.

15. The method of claim 1, wherein the virus causes systemic symptoms on *Solanum lycopersicum* plants homozygous for Tm1, Tm2, and $Tm2^2$.

16. The method of claim 1, wherein the method identifies one or more plants comprising resistance against a tobamovirus whose genome comprises at least 97% sequence identity to SEQ ID NO: 1.

17. The method of claim 1, wherein the method identifies one or more plants comprising resistance against a tobamovirus whose genome comprises at least 99% sequence identity to SEQ ID NO: 1.

18. The method of claim 14, wherein the method identifies one or more plants comprising resistance against a tobamovirus whose genome comprises at least 97% sequence identity to SEQ ID NO: 1.

19. The method of claim 14, wherein the method identifies one or more plants comprising resistance against a tobamovirus whose genome comprises at least 99% sequence identity to SEQ ID NO: 1.

20. The method of claim 15, wherein the method identifies one or more plants comprising resistance against a tobamovirus whose genome comprises at least 97% sequence identity to SEQ ID NO: 1.

21. The method of claim 15, wherein the method identifies one or more plants comprising resistance against a tobamovirus whose genome comprises at least 99% sequence identity to SEQ ID NO: 1.

* * * * *

SEQUENCE LISTING

```
<160> NUMBER OF SEQ ID NOS: 10

<210> SEQ ID NO 1
<211> LENGTH: 6402
<212> TYPE: DNA
<213> ORGANISM: unknown
<220> FEATURE:
<223> OTHER INFORMATION: genome of new tobamovirus
<220> FEATURE:
<221> NAME/KEY: exon
<222> LOCATION: (77)..(3424)
<223> OTHER INFORMATION: ORF1 = p126
<220> FEATURE:
<221> NAME/KEY: exon
<222> LOCATION: (4911)..(5708)
<223> OTHER INFORMATION: ORF3 = Movement protein

<400> SEQUENCE: 1

gtatttttgt tttacaacat ataccaacaa caacaaacaa caaacaacaa cattacaatt     60
```

-continued

```
actatttaca actaca atg gca tac aca cag aca gct acc aca tcc gct ttg     112
                  Met Ala Tyr Thr Gln Thr Ala Thr Thr Ser Ala Leu
                  1               5                   10

ctc gac act gtc cga ggt aac aat acc ttg gtc aat gat ctt gcg aag       160
Leu Asp Thr Val Arg Gly Asn Asn Thr Leu Val Asn Asp Leu Ala Lys
        15                  20                  25

cgg cgt ctt tat gac aca gcg gtc gac gag ttc aac gct cgt gat cgc       208
Arg Arg Leu Tyr Asp Thr Ala Val Asp Glu Phe Asn Ala Arg Asp Arg
    30                  35                  40

agg ccc aaa gta aat ttt tcc aaa gta ata agt gag gaa cag acg ctt       256
Arg Pro Lys Val Asn Phe Ser Lys Val Ile Ser Glu Glu Gln Thr Leu
45                  50                  55                  60

att gct act agg gca tat cca gaa ttc cag ata acc ttc tat aat acg       304
Ile Ala Thr Arg Ala Tyr Pro Glu Phe Gln Ile Thr Phe Tyr Asn Thr
                65                  70                  75

cag aac gcc gtg cat tcg ctt gcc ggt gga cta cga tcc tta gaa ctg       352
Gln Asn Ala Val His Ser Leu Ala Gly Gly Leu Arg Ser Leu Glu Leu
            80                  85                  90

gaa tat cta atg atg cag atc ccg tac gga tca ctc aca tat gat ata       400
Glu Tyr Leu Met Met Gln Ile Pro Tyr Gly Ser Leu Thr Tyr Asp Ile
        95                  100                 105

ggt ggg aat ttt gca tct cat ctg ttc aaa gga cgg gca tat gtt cac       448
Gly Gly Asn Phe Ala Ser His Leu Phe Lys Gly Arg Ala Tyr Val His
    110                 115                 120

tgc tgt atg ccc aat ctt gat gtc cgc gac ata atg cgg cac gaa ggc       496
Cys Cys Met Pro Asn Leu Asp Val Arg Asp Ile Met Arg His Glu Gly
125                 130                 135                 140

cag aaa gac agt ata gaa tta tac ctt tcc agg ctt gag cgg ggc aac       544
Gln Lys Asp Ser Ile Glu Leu Tyr Leu Ser Arg Leu Glu Arg Gly Asn
                145                 150                 155

aaa gtt gtc cca aat ttc caa aag gaa gct ctt gac aga tac gct gaa       592
Lys Val Val Pro Asn Phe Gln Lys Glu Ala Leu Asp Arg Tyr Ala Glu
            160                 165                 170

acg cca gac gaa gtt gtc tgt cac agt acc ttc caa acg tgt acg cac       640
Thr Pro Asp Glu Val Val Cys His Ser Thr Phe Gln Thr Cys Thr His
        175                 180                 185

cag cag gtg gaa aac aca ggc agg gtg tat gct att gca ttg cac agt       688
Gln Gln Val Glu Asn Thr Gly Arg Val Tyr Ala Ile Ala Leu His Ser
    190                 195                 200

ata tac gat ata cct gct gat gaa ttc gga gcg gca ctt tta agg aaa       736
Ile Tyr Asp Ile Pro Ala Asp Glu Phe Gly Ala Ala Leu Leu Arg Lys
205                 210                 215                 220

aat gtc cat gtt tgt tac gcc gcc ttc cac ttt tcc gag aat tta ctt       784
Asn Val His Val Cys Tyr Ala Ala Phe His Phe Ser Glu Asn Leu Leu
                225                 230                 235

ctc gaa gat tca cac gtc aac ctt gac gaa atc aac gcg tgt ttt tcg       832
Leu Glu Asp Ser His Val Asn Leu Asp Glu Ile Asn Ala Cys Phe Ser
            240                 245                 250

cgt gat gga gac aag ctg act ttt tct ttc gca tct gag agc act tta       880
Arg Asp Gly Asp Lys Leu Thr Phe Ser Phe Ala Ser Glu Ser Thr Leu
        255                 260                 265

aat tat tgt cat agt tat tct aat att tta aaa tac gtg tgc aaa act       928
Asn Tyr Cys His Ser Tyr Ser Asn Ile Leu Lys Tyr Val Cys Lys Thr
    270                 275                 280

tac ttc ccg gca tct aat aga gag gtc tac atg aag gag ttt ttg gtc       976
Tyr Phe Pro Ala Ser Asn Arg Glu Val Tyr Met Lys Glu Phe Leu Val
285                 290                 295                 300

acc agg gtt aac acc tgg ttt tgt aag ttt tct agg ata gat act ttt      1024
Thr Arg Val Asn Thr Trp Phe Cys Lys Phe Ser Arg Ile Asp Thr Phe
                305                 310                 315
```

-continued

```
tta tta tac aag ggg gta gcc cac aaa ggt gta aat agt gag caa ttt      1072
Leu Leu Tyr Lys Gly Val Ala His Lys Gly Val Asn Ser Glu Gln Phe
            320                 325                 330

tac agc gca atg gaa gat gca tgg cac tac aaa aag act ctt gca atg      1120
Tyr Ser Ala Met Glu Asp Ala Trp His Tyr Lys Lys Thr Leu Ala Met
        335                 340                 345

tgt aac agc gag agg att ctt ctt gaa gat tcc tca tcg gtc aat tac      1168
Cys Asn Ser Glu Arg Ile Leu Leu Glu Asp Ser Ser Ser Val Asn Tyr
    350                 355                 360

tgg ttc cca aaa atg aga gat atg gtc ata gtt cct cta ttc gac ata      1216
Trp Phe Pro Lys Met Arg Asp Met Val Ile Val Pro Leu Phe Asp Ile
365                 370                 375                 380

tct ctc gac acc agt aaa agg acc cgc aaa gaa gtc tta gtg tca aag      1264
Ser Leu Asp Thr Ser Lys Arg Thr Arg Lys Glu Val Leu Val Ser Lys
                385                 390                 395

gat ttt gta ttc aca gtt tta aat cac att cgc act tat caa gcc aag      1312
Asp Phe Val Phe Thr Val Leu Asn His Ile Arg Thr Tyr Gln Ala Lys
            400                 405                 410

gca ctt aca tac tcc aat gtt tta tcc ttt gtc gaa tca att cgt tca      1360
Ala Leu Thr Tyr Ser Asn Val Leu Ser Phe Val Glu Ser Ile Arg Ser
        415                 420                 425

agg gta att atc aac gga gtg act gcc agg tct gag tgg gat gtt gac      1408
Arg Val Ile Ile Asn Gly Val Thr Ala Arg Ser Glu Trp Asp Val Asp
    430                 435                 440

aaa tct ctt ttg caa tcc ttg tcc atg aca ttt ttc ttg cat act aag      1456
Lys Ser Leu Leu Gln Ser Leu Ser Met Thr Phe Phe Leu His Thr Lys
445                 450                 455                 460

ctt gcc gtt tta aaa gac gaa ttg tta atc agc aag ttt agt ttg ggg      1504
Leu Ala Val Leu Lys Asp Glu Leu Leu Ile Ser Lys Phe Ser Leu Gly
                465                 470                 475

cca aaa tca gta agc cag cat gta tgg gat gag att tcc ctg gct ttt      1552
Pro Lys Ser Val Ser Gln His Val Trp Asp Glu Ile Ser Leu Ala Phe
            480                 485                 490

gga aac gca ttt cca tcg atc aag gag aga ctg cta aat cgg aaa cta      1600
Gly Asn Ala Phe Pro Ser Ile Lys Glu Arg Leu Leu Asn Arg Lys Leu
        495                 500                 505

att aaa gtg tcg gga gac gca tta gaa atc agg gtg cct gat tta tat      1648
Ile Lys Val Ser Gly Asp Ala Leu Glu Ile Arg Val Pro Asp Leu Tyr
    510                 515                 520

gtg act ttt cac gat aga tta gtg act gag tac aaa aca tcg gtg gat      1696
Val Thr Phe His Asp Arg Leu Val Thr Glu Tyr Lys Thr Ser Val Asp
525                 530                 535                 540

atg cca gtg ctt gat atc aga aag aga atg gag gag act gag gtt atg      1744
Met Pro Val Leu Asp Ile Arg Lys Arg Met Glu Glu Thr Glu Val Met
                545                 550                 555

tac aat gca ttg tct gag cta tct gtg ctc aag gag tcg gac aag ttc      1792
Tyr Asn Ala Leu Ser Glu Leu Ser Val Leu Lys Glu Ser Asp Lys Phe
            560                 565                 570

gac gct gat gtt ttt tcc cgg atg tgc cag act ttg gag gta gac cca      1840
Asp Ala Asp Val Phe Ser Arg Met Cys Gln Thr Leu Glu Val Asp Pro
        575                 580                 585

atg act gca gca aag gtt att gtg gca gtg atg agc aac gag agc gga      1888
Met Thr Ala Ala Lys Val Ile Val Ala Val Met Ser Asn Glu Ser Gly
    590                 595                 600

ctg act ctt aca ttc gaa cag cca act gaa gca aat gtc gca ttg gca      1936
Leu Thr Leu Thr Phe Glu Gln Pro Thr Glu Ala Asn Val Ala Leu Ala
605                 610                 615                 620

ctt aaa gat tca gaa aaa gcc tct gag ggt gca cta gtg gtt act tct      1984
Leu Lys Asp Ser Glu Lys Ala Ser Glu Gly Ala Leu Val Val Thr Ser
```

-continued

```
                625                 630                 635

aga gat gtt gaa gaa cca tcc atg aag ggt tca atg gca aga gga gag     2032
Arg Asp Val Glu Glu Pro Ser Met Lys Gly Ser Met Ala Arg Gly Glu
            640                 645                 650

tta caa ttg gcc ggt ctg tct gga gac caa cca gag tct tcc tat act     2080
Leu Gln Leu Ala Gly Leu Ser Gly Asp Gln Pro Glu Ser Ser Tyr Thr
        655                 660                 665

cgg aac gag gaa ata gag tca tta gag caa ttc cac atg gca acg gct     2128
Arg Asn Glu Glu Ile Glu Ser Leu Glu Gln Phe His Met Ala Thr Ala
    670                 675                 680

agt tcg tta att cgg aaa cag atg agt tcg att gtg tac acg ggc ccc     2176
Ser Ser Leu Ile Arg Lys Gln Met Ser Ser Ile Val Tyr Thr Gly Pro
685                 690                 695                 700

att aaa gtt cag caa atg aaa aac ttt att gat agc ctg gta gca tca     2224
Ile Lys Val Gln Gln Met Lys Asn Phe Ile Asp Ser Leu Val Ala Ser
                705                 710                 715

ctc tct gct gcg gtg tcg aac cta gtc aag atc cta aag gat aca gct     2272
Leu Ser Ala Ala Val Ser Asn Leu Val Lys Ile Leu Lys Asp Thr Ala
            720                 725                 730

gct ata gat ctc gaa acc cgt cag aag ttt gga gtc tta gat gtt gcg     2320
Ala Ile Asp Leu Glu Thr Arg Gln Lys Phe Gly Val Leu Asp Val Ala
        735                 740                 745

acc aaa aga tgg tta att aaa cct tta gcc aag aat cac gca tgg ggc     2368
Thr Lys Arg Trp Leu Ile Lys Pro Leu Ala Lys Asn His Ala Trp Gly
    750                 755                 760

gtt att gaa aca cat gct agg aag tac cac gtt gca ctt ttg gag tat     2416
Val Ile Glu Thr His Ala Arg Lys Tyr His Val Ala Leu Leu Glu Tyr
765                 770                 775                 780

gat gag cat gga gtg gta act tgc gac agt tgg aga agg gtg gcc gtg     2464
Asp Glu His Gly Val Val Thr Cys Asp Ser Trp Arg Arg Val Ala Val
                785                 790                 795

agt tct gag tca atg gtt tat tct gat atg gcg aag ctc aga aca ctg     2512
Ser Ser Glu Ser Met Val Tyr Ser Asp Met Ala Lys Leu Arg Thr Leu
            800                 805                 810

agg aga tta tta aga gat ggt gag cct cat gtc agc agt gct aaa gtc     2560
Arg Arg Leu Leu Arg Asp Gly Glu Pro His Val Ser Ser Ala Lys Val
        815                 820                 825

gtc cta gtt gac ggt gtc ccg ggt tgt gga aag aca aaa gag att ctc     2608
Val Leu Val Asp Gly Val Pro Gly Cys Gly Lys Thr Lys Glu Ile Leu
    830                 835                 840

tcg aaa gta aat ttt gag gaa gat cta atc tta gta ccg ggt aag cag     2656
Ser Lys Val Asn Phe Glu Glu Asp Leu Ile Leu Val Pro Gly Lys Gln
845                 850                 855                 860

gct gct gaa atg ata aag agg cgt gct aat gcg tca gga ata att caa     2704
Ala Ala Glu Met Ile Lys Arg Arg Ala Asn Ala Ser Gly Ile Ile Gln
                865                 870                 875

gcc aca aga gat aat gtt cgt act gtt gat tca ttt ata atg aat tac     2752
Ala Thr Arg Asp Asn Val Arg Thr Val Asp Ser Phe Ile Met Asn Tyr
            880                 885                 890

ggt aaa gga aca cgc tgt cag ttc aaa agg tta ttt atc gac gaa ggt     2800
Gly Lys Gly Thr Arg Cys Gln Phe Lys Arg Leu Phe Ile Asp Glu Gly
        895                 900                 905

ctg atg ttg cac act ggt tgt gtg aat ttt ctt gtt tct atg tct ctg     2848
Leu Met Leu His Thr Gly Cys Val Asn Phe Leu Val Ser Met Ser Leu
    910                 915                 920

tgc gaa att gca tat gtt tat gga gac aca caa caa att cca tac atc     2896
Cys Glu Ile Ala Tyr Val Tyr Gly Asp Thr Gln Gln Ile Pro Tyr Ile
925                 930                 935                 940

aac aga gta tcc ggt ttt ccg tac cct gca cat ttt gca aaa ata gag     2944
```

-continued

```
Asn Arg Val Ser Gly Phe Pro Tyr Pro Ala His Phe Ala Lys Ile Glu
                945                 950                 955

gtt gat gag gtg gaa act cgc aga act acg ctg cgt tgt cca gcc gac     2992
Val Asp Glu Val Glu Thr Arg Arg Thr Thr Leu Arg Cys Pro Ala Asp
            960                 965                 970

att acc cac tat ctt aac aga agg tac gaa gga tat gtc atg tgt aca     3040
Ile Thr His Tyr Leu Asn Arg Arg Tyr Glu Gly Tyr Val Met Cys Thr
        975                 980                 985

tcg tcg gtt aaa aag tca gtt tct cag gaa atg gtg  agc ggg gcc gca    3088
Ser Ser Val Lys Lys Ser Val Ser Gln Glu Met Val  Ser Gly Ala Ala
    990                 995                 1000

atg  atc aat cct gta tct  aag cca ttg aat ggg  aaa gtt ttg act      3133
Met  Ile Asn Pro Val Ser  Lys Pro Leu Asn Gly  Lys Val Leu Thr
1005                 1010                 1015

ttc  act cag tct gat aaa  gag gcg ctg ctt tct  cga gga tat acg      3178
Phe  Thr Gln Ser Asp Lys  Glu Ala Leu Leu Ser  Arg Gly Tyr Thr
1020                 1025                 1030

gac  gtc cat aca gta cat  gag gta caa ggt gag  aca tat gca gat      3223
Asp  Val His Thr Val His  Glu Val Gln Gly Glu  Thr Tyr Ala Asp
1035                 1040                 1045

gtg  tcg ttg gtc aga ttg  act ccg aca cct gta  tct atc atc gca      3268
Val  Ser Leu Val Arg Leu  Thr Pro Thr Pro Val  Ser Ile Ile Ala
1050                 1055                 1060

gga  gat agt ccg cac gtt  ctc gta gct ttg tca  agg cat acc caa      3313
Gly  Asp Ser Pro His Val  Leu Val Ala Leu Ser  Arg His Thr Gln
1065                 1070                 1075

aca  ttg aag tat tac acc  gta gtg atg gat cct  ctt gta agt ata      3358
Thr  Leu Lys Tyr Tyr Thr  Val Val Met Asp Pro  Leu Val Ser Ile
1080                 1085                 1090

att  agg gat tta gaa aaa  ctt agt tct tac ttg  tta gat atg tat      3403
Ile  Arg Asp Leu Glu Lys  Leu Ser Ser Tyr Leu  Leu Asp Met Tyr
1095                 1100                 1105

aaa  gta gat gca ggg acc  caa tagcaattac aggtagactc cgtgtttaaa      3454
Lys  Val Asp Ala Gly Thr  Gln
1110                 1115

ggttctaatc tttttgttgc agcaccaaag actggagata tctcagatat gcaattttac   3514

tatgataagt gtctcccagg taatagcacc atgttaaata actatgatgc tgttaccatg   3574

aggttgactg acatttctct taatgtcaaa gattgcatat tggatttctc taagtctgtg   3634

gctgcaccga aggatccgat caaaccactg attccaatgg tacgaacagc ggcagaaatg   3694

ccacgccaga ctggactatt ggaaaatttg gtggcgatga tcaaaagaaa ctttaattca   3754

ccggagttat caggaataat cgacattgag aatactgcat ctttagtagt agataaattt   3814

tttgatagtt acttgcttaa agaaaaaaga aaaccaaata aaaatgtttc tttattttgt   3874

agagagtctc tcaatagatg gttagagaag caggagcaag tgaccattgg tcagcttgca   3934

gattttgatt ttgtggatct tcctgccgtt gatcagtaca ggcatatgat taaagcgcaa   3994

cctaagcaga agctggatac atcaattcaa agcgaatatc cggccttgca gacgattgtg   4054

tatcattcga aaaagatcaa cgcaatcttc ggtcctttgt tcagtgagct cacaaggcaa   4114

atgctcgaaa gcatagactc aagtaagttt ttgttcttta caaggaagac gccagctcaa   4174

attgaggatt tcttcggaga tctcgatagc catgtcccta tggatatctt ggagttggat   4234

atttcgaagt atgacaaatc tcagaacgag ttccactgtg cagtagagta tgaaatatgg   4294

agaagacttg gattagaaga ttttctggga gaagtttgga aacaaggcca taggaaaact   4354

actcttaaag attacacagc tggtattaaa acgtgtttat ggtaccagag aaagagtggg   4414
```

-continued

```
gacgttacaa cattcatcgg taatacggtg attattgctg cttgtttagc ttccatgttg   4474

cccatggaga aaataatcaa aggtgcattt tgcggagatg acagtttact atacttccca   4534

aaaggttgtg agtttcctga catacagcat acagccaacc ttatgtggaa tttcgaggct   4594

aagctattca gaaagcagta tggttatttc tgtggaaggt acgtgataca tcatgacaga   4654

gggtgtattg tttattatga ccctttgaag ttgatttcta aacttggtgc taaacacatc   4714

aaggattggg atcacttaga agagttcaga agatcccttt gtgatgttgc aaattcgttg   4774

aacaactgtg cgtattacac gcagttggac gacgctgtga gtgaggtcca taaaaccgca   4834

cccccgggtt cgtctgtata taaaagttta gttaaatatc tgtccgataa ggttcttttt   4894

agaagtttgt ttatag atg gct ctt gtt  aag ggt aaa gtc aat  att aat     4943
                  Met Ala Leu Val  Lys Gly Lys Val Asn  Ile Asn
                              1120                 1125

gag ttc ata  gac ttg tca aaa tca  gaa aaa ttt ctt ccg  tct atg      4988
Glu Phe Ile  Asp Leu Ser Lys Ser  Glu Lys Phe Leu Pro  Ser Met
        1130                 1135                 1140

ttc aca cct  gtt aag agt gtc atg  atc tcc aag gtt gat  aag ata      5033
Phe Thr Pro  Val Lys Ser Val Met  Ile Ser Lys Val Asp  Lys Ile
        1145                 1150                 1155

ttg gtt cat  gaa gat gaa tct ttg  tcc gaa gtc aat tta  ctc aaa      5078
Leu Val His  Glu Asp Glu Ser Leu  Ser Glu Val Asn Leu  Leu Lys
        1160                 1165                 1170

ggt gta aaa  ctc att gat ggt ggc  tat gta cat ctt gct  ggt ctt      5123
Gly Val Lys  Leu Ile Asp Gly Gly  Tyr Val His Leu Ala  Gly Leu
        1175                 1180                 1185

gtg gtg aca  ggt gaa tgg aat ttg  cca gat aat tgt cgt  ggt ggt      5168
Val Val Thr  Gly Glu Trp Asn Leu  Pro Asp Asn Cys Arg  Gly Gly
        1190                 1195                 1200

gtc agt gtc  tgt ttg gtc gat aag  aga atg gag aga gcg  gac gag      5213
Val Ser Val  Cys Leu Val Asp Lys  Arg Met Glu Arg Ala  Asp Glu
        1205                 1210                 1215

gca act ctt  gct tca tac tat acc  gca gcg gct aag aaa  agg ttt      5258
Ala Thr Leu  Ala Ser Tyr Tyr Thr  Ala Ala Ala Lys Lys  Arg Phe
        1220                 1225                 1230

cag ttc aaa  gtc gtt cca aat tac  aac atc act acc aag  gac gca      5303
Gln Phe Lys  Val Val Pro Asn Tyr  Asn Ile Thr Thr Lys  Asp Ala
        1235                 1240                 1245

gaa aag gca  gtt tgg caa gta cta  gtt aat att aga aat  gtt aaa      5348
Glu Lys Ala  Val Trp Gln Val Leu  Val Asn Ile Arg Asn  Val Lys
        1250                 1255                 1260

att gct gcg  ggt tac tgt ccg ctg  tca tta gaa ttt gtg  tca gtg      5393
Ile Ala Ala  Gly Tyr Cys Pro Leu  Ser Leu Glu Phe Val  Ser Val
        1265                 1270                 1275

tgt att gtt  tat aaa aat att ata  aaa ctc ggt ttg aga  gag aaa      5438
Cys Ile Val  Tyr Lys Asn Ile Ile  Lys Leu Gly Leu Arg  Glu Lys
        1280                 1285                 1290

att acg agc  gtc acg gat gga ggg  ccc atg gaa cta tca  gaa gaa      5483
Ile Thr Ser  Val Thr Asp Gly Gly  Pro Met Glu Leu Ser  Glu Glu
        1295                 1300                 1305

gtt gtt gat  gag ttc atg gaa gaa  gtc ccg atg tct gta  agg ctt      5528
Val Val Asp  Glu Phe Met Glu Glu  Val Pro Met Ser Val  Arg Leu
        1310                 1315                 1320

gca aaa ttt  cgt tcg aag acc gga  aaa aag ttt agt agt  aaa agt      5573
Ala Lys Phe  Arg Ser Lys Thr Gly  Lys Lys Phe Ser Ser  Lys Ser
        1325                 1330                 1335

gag aat aat  agt ggt aat aat agg  ccg aaa cca gac aaa  aac caa      5618
Glu Asn Asn  Ser Gly Asn Asn Arg  Pro Lys Pro Asp Lys  Asn Gln
        1340                 1345                 1350
```

-continued

```
agg aag gga  aag ggt tta aaa gtt  agg gtt gag aag gat  aat tta      5663
Arg Lys Gly  Lys Gly Leu Lys Val  Arg Val Glu Lys Asp  Asn Leu
        1355                1360                1365

att gat aat  gaa ttg gag act tac  gtc gcc gat tca gat  tcg tat      5708
Ile Asp Asn  Glu Leu Glu Thr Tyr  Val Ala Asp Ser Asp  Ser Tyr
        1370                1375                1380

taaatattta aatatgtctt acacaatcgc aactccatcg caatttgtgt ttttgtcatc   5768

agcatgggcc gaccctatag aattaataaa tttatgtact aattcactag gtaatcagtt   5828

ccaaacacaa caagctagaa caaccgttca acggcaattt agcgaagtgt ggaaacctgt   5888

ccctcaagtc actgttaggt ttcctgacag tggttttaag gtgtataggt acaatgcggt   5948

actagatcct ctagttactg ctttgttagg agctttcgat actagaaata ggattataga   6008

agtcgaaaat caggcgaacc cgacaaccgc cgaaacgtta gacgctactc gtagagtaga   6068

tgacgcaacg gtggctataa ggagcgctat aaataattta gtagtagaat tggtcaaagg   6128

aacaggtttg tacaatcaga gcacatttga aagtgcatcc ggtttacaat ggtcctctgc   6188

acctgcatct tgagataatc gagatgctta aataacagat tgtgtctgca aacacacgtg   6248

gtacgtacga taacgtatag tgtttttccc tccacttaaa tcgaagggta gtgtcttgga   6308

gcgcgcggga caaatgtgta tggttcatac acatccgtag gcacgtaata aagcgaggga   6368

ttcgaattcc cccggaaccc ccggtagggg ccca                               6402


<210> SEQ ID NO 2
<211> LENGTH: 6402
<212> TYPE: DNA
<213> ORGANISM: unknown
<220> FEATURE:
<223> OTHER INFORMATION: genome of new tobamovirus
<220> FEATURE:
<221> NAME/KEY: exon
<222> LOCATION: (3446)..(4921)
<223> OTHER INFORMATION: ORF2 (p183) final 492 amino acids
<220> FEATURE:
<221> NAME/KEY: exon
<222> LOCATION: (5671)..(6198)
<223> OTHER INFORMATION: ORF4 = Coat Protein

<400> SEQUENCE: 2

gtatttttgt tttacaacat ataccaacaa caacaaacaa caaacaacaa cattacaatt     60

actatttaca actacaatgg catacacaca gacagctacc acatccgctt tgctcgacac    120

tgtccgaggt aacaatacct tggtcaatga tcttgcgaag cggcgtcttt atgacacagc    180

ggtcgacgag ttcaacgctc gtgatcgcag gcccaaagta aatttttcca aagtaataag    240

tgaggaacag acgcttattg ctactagggc atatccagaa ttccagataa ccttctataa    300

tacgcagaac gccgtgcatt cgcttgccgg tggactacga tccttagaac tggaatatct    360

aatgatgcag atcccgtacg gatcactcac atatgatata ggtgggaatt ttgcatctca    420

tctgttcaaa ggacgggcat atgttcactg ctgtatgccc aatcttgatg tccgcgacat    480

aatgcggcac gaaggccaga aagacagtat agaattatac ctttccaggc ttgagcgggg    540

caacaaagtt gtcccaaatt tccaaaagga agctcttgac agatacgctg aaacgccaga    600

cgaagttgtc tgtcacagta ccttccaaac gtgtacgcac cagcaggtgg aaaacacagg    660

cagggtgtat gctattgcat tgcacagtat atacgatata cctgctgatg aattcggagc    720

ggcactttta aggaaaaatg tccatgtttg ttacgccgcc ttccactttt ccgagaattt    780

acttctcgaa gattcacacg tcaaccttga cgaaatcaac gcgtgttttt cgcgtgatgg    840
```

-continued

```
agacaagctg actttttctt tcgcatctga gagcacttta aattattgtc atagttattc    900
taatatttta aaatacgtgt gcaaaactta cttcccggca tctaatagag aggtctacat    960
gaaggagttt ttggtcacca gggttaacac ctggttttgt aagttttcta ggatagatac   1020
tttttttatta tacaaggggg tagcccacaa aggtgtaaat agtgagcaat tttacagcgc   1080
aatggaagat gcatggcact acaaaaagac tcttgcaatg tgtaacagcg agaggattct   1140
tcttgaagat tcctcatcgg tcaattactg gttcccaaaa atgagagata tggtcatagt   1200
tcctctattc gacatatctc tcgacaccag taaaaggacc cgcaaagaag tcttagtgtc   1260
aaaggatttt gtattcacag ttttaaatca cattcgcact tatcaagcca aggcacttac   1320
atactccaat gttttatcct ttgtcgaatc aattcgttca agggtaatta tcaacggagt   1380
gactgccagg tctgagtggg atgttgacaa atctcttttg caatccttgt ccatgacatt   1440
tttcttgcat actaagcttg ccgttttaaa agacgaattg ttaatcagca agtttagttt   1500
ggggccaaaa tcagtaagcc agcatgtatg ggatgagatt tccctggctt ttggaaacgc   1560
atttccatcg atcaaggaga gactgctaaa tcggaaacta attaaagtgt cgggagacgc   1620
attagaaatc agggtgcctg atttatatgt gacttttcac gatagattag tgactgagta   1680
caaaacatcg gtggatatgc cagtgcttga tatcagaaag agaatggagg agactgaggt   1740
tatgtacaat gcattgtctg agctatctgt gctcaaggag tcggacaagt tcgacgctga   1800
tgttttttcc cggatgtgcc agactttgga ggtagaccca atgactgcag caaaggttat   1860
tgtggcagtg atgagcaacg agagcggact gactcttaca ttcgaacagc caactgaagc   1920
aaatgtcgca ttggcactta aagattcaga aaaagcctct gagggtgcac tagtggttac   1980
ttctagagat gttgaagaac catccatgaa gggttcaatg gcaagaggag agttacaatt   2040
ggccggtctg tctggagacc aaccagagtc ttcctatact cggaacgagg aaatagagtc   2100
attagagcaa ttccacatgg caacggctag ttcgttaatt cggaaacaga tgagttcgat   2160
tgtgtacacg ggccccatta aagttcagca aatgaaaaac tttattgata gcctggtagc   2220
atcactctct gctgcggtgt cgaacctagt caagatccta aaggatacag ctgctataga   2280
tctcgaaacc cgtcagaagt ttggagtctt agatgttgcg accaaaagat ggttaattaa   2340
acctttagcc aagaatcacg catggggcgt tattgaaaca catgctagga agtaccacgt   2400
tgcacttttg gagtatgatg agcatggagt ggtaacttgc gacagttgga gaagggtggc   2460
cgtgagttct gagtcaatgg tttattctga tatggcgaag ctcagaacac tgaggagatt   2520
attaagagat ggtgagcctc atgtcagcag tgctaaagtc gtcctagttg acggtgtccc   2580
gggttgtgga aagacaaaag agattctctc gaaagtaaat tttgaggaag atctaatctt   2640
agtaccgggt aagcaggctg ctgaaatgat aaagaggcgt gctaatgcgt caggaataat   2700
tcaagccaca agagataatg ttcgtactgt tgattcattt ataatgaatt acggtaaagg   2760
aacacgctgt cagttcaaaa ggttatttat cgacgaaggt ctgatgttgc acactggttg   2820
tgtgaatttt cttgtttcta tgtctctgtg cgaaattgca tatgtttatg gagacacaca   2880
acaaattcca tacatcaaca gagtatccgg ttttccgtac cctgcacatt ttgcaaaaat   2940
agaggttgat gaggtggaaa ctcgcagaac tacgctgcgt tgtccagccg acattaccca   3000
ctatcttaac agaaggtacg aaggatatgt catgtgtaca tcgtcggtta aaaagtcagt   3060
ttctcaggaa atggtgagcg gggccgcaat gatcaatcct gtatctaagc cattgaatgg   3120
gaaagttttg actttcactc agtctgataa agaggcgctg ctttctcgag gatatacgga   3180
cgtccataca gtacatgagg tacaaggtga gacatatgca gatgtgtcgt tggtcagatt   3240
```

-continued

```
gactccgaca cctgtatcta tcatcgcagg agatagtccg cacgttctcg tagctttgtc   3300

aaggcatacc caaacattga agtattacac cgtagtgatg gatcctcttg taagtataat   3360

tagggattta gaaaaactta gttcttactt gttagatatg tataaagtag atgcagggac   3420

ccaatagcaa ttacaggtag actcc gtg ttt aaa ggt tct aat ctt ttt gtt     3472
                            Val Phe Lys Gly Ser Asn Leu Phe Val
                            1               5

gca gca cca aag act gga gat atc tca gat atg caa ttt tac tat gat     3520
Ala Ala Pro Lys Thr Gly Asp Ile Ser Asp Met Gln Phe Tyr Tyr Asp
10              15                  20                  25

aag tgt ctc cca ggt aat agc acc atg tta aat aac tat gat gct gtt     3568
Lys Cys Leu Pro Gly Asn Ser Thr Met Leu Asn Asn Tyr Asp Ala Val
                30                  35                  40

acc atg agg ttg act gac att tct ctt aat gtc aaa gat tgc ata ttg     3616
Thr Met Arg Leu Thr Asp Ile Ser Leu Asn Val Lys Asp Cys Ile Leu
            45                  50                  55

gat ttc tct aag tct gtg gct gca ccg aag gat ccg atc aaa cca ctg     3664
Asp Phe Ser Lys Ser Val Ala Ala Pro Lys Asp Pro Ile Lys Pro Leu
        60                  65                  70

att cca atg gta cga aca gcg gca gaa atg cca cgc cag act gga cta     3712
Ile Pro Met Val Arg Thr Ala Ala Glu Met Pro Arg Gln Thr Gly Leu
    75                  80                  85

ttg gaa aat ttg gtg gcg atg atc aaa aga aac ttt aat tca ccg gag     3760
Leu Glu Asn Leu Val Ala Met Ile Lys Arg Asn Phe Asn Ser Pro Glu
90                  95                  100                 105

tta tca gga ata atc gac att gag aat act gca tct tta gta gta gat     3808
Leu Ser Gly Ile Ile Asp Ile Glu Asn Thr Ala Ser Leu Val Val Asp
                110                 115                 120

aaa ttt ttt gat agt tac ttg ctt aaa gaa aaa aga aaa cca aat aaa     3856
Lys Phe Phe Asp Ser Tyr Leu Leu Lys Glu Lys Arg Lys Pro Asn Lys
            125                 130                 135

aat gtt tct tta ttt tgt aga gag tct ctc aat aga tgg tta gag aag     3904
Asn Val Ser Leu Phe Cys Arg Glu Ser Leu Asn Arg Trp Leu Glu Lys
        140                 145                 150

cag gag caa gtg acc att ggt cag ctt gca gat ttt gat ttt gtg gat     3952
Gln Glu Gln Val Thr Ile Gly Gln Leu Ala Asp Phe Asp Phe Val Asp
    155                 160                 165

ctt cct gcc gtt gat cag tac agg cat atg att aaa gcg caa cct aag     4000
Leu Pro Ala Val Asp Gln Tyr Arg His Met Ile Lys Ala Gln Pro Lys
170                 175                 180                 185

cag aag ctg gat aca tca att caa agc gaa tat ccg gcc ttg cag acg     4048
Gln Lys Leu Asp Thr Ser Ile Gln Ser Glu Tyr Pro Ala Leu Gln Thr
                190                 195                 200

att gtg tat cat tcg aaa aag atc aac gca atc ttc ggt cct ttg ttc     4096
Ile Val Tyr His Ser Lys Lys Ile Asn Ala Ile Phe Gly Pro Leu Phe
            205                 210                 215

agt gag ctc aca agg caa atg ctc gaa agc ata gac tca agt aag ttt     4144
Ser Glu Leu Thr Arg Gln Met Leu Glu Ser Ile Asp Ser Ser Lys Phe
        220                 225                 230

ttg ttc ttt aca agg aag acg cca gct caa att gag gat ttc ttc gga     4192
Leu Phe Phe Thr Arg Lys Thr Pro Ala Gln Ile Glu Asp Phe Phe Gly
    235                 240                 245

gat ctc gat agc cat gtc cct atg gat atc ttg gag ttg gat att tcg     4240
Asp Leu Asp Ser His Val Pro Met Asp Ile Leu Glu Leu Asp Ile Ser
250                 255                 260                 265

aag tat gac aaa tct cag aac gag ttc cac tgt gca gta gag tat gaa     4288
Lys Tyr Asp Lys Ser Gln Asn Glu Phe His Cys Ala Val Glu Tyr Glu
                270                 275                 280
```

-continued

```
ata tgg aga aga ctt gga tta gaa gat ttt ctg gga gaa gtt tgg aaa     4336
Ile Trp Arg Arg Leu Gly Leu Glu Asp Phe Leu Gly Glu Val Trp Lys
            285                 290                 295

caa ggc cat agg aaa act act ctt aaa gat tac aca gct ggt att aaa     4384
Gln Gly His Arg Lys Thr Thr Leu Lys Asp Tyr Thr Ala Gly Ile Lys
        300                 305                 310

acg tgt tta tgg tac cag aga aag agt ggg gac gtt aca aca ttc atc     4432
Thr Cys Leu Trp Tyr Gln Arg Lys Ser Gly Asp Val Thr Thr Phe Ile
    315                 320                 325

ggt aat acg gtg att att gct gct tgt tta gct tcc atg ttg ccc atg     4480
Gly Asn Thr Val Ile Ile Ala Ala Cys Leu Ala Ser Met Leu Pro Met
330                 335                 340                 345

gag aaa ata atc aaa ggt gca ttt tgc gga gat gac agt tta cta tac     4528
Glu Lys Ile Ile Lys Gly Ala Phe Cys Gly Asp Asp Ser Leu Leu Tyr
                350                 355                 360

ttc cca aaa ggt tgt gag ttt cct gac ata cag cat aca gcc aac ctt     4576
Phe Pro Lys Gly Cys Glu Phe Pro Asp Ile Gln His Thr Ala Asn Leu
            365                 370                 375

atg tgg aat ttc gag gct aag cta ttc aga aag cag tat ggt tat ttc     4624
Met Trp Asn Phe Glu Ala Lys Leu Phe Arg Lys Gln Tyr Gly Tyr Phe
        380                 385                 390

tgt gga agg tac gtg ata cat cat gac aga ggg tgt att gtt tat tat     4672
Cys Gly Arg Tyr Val Ile His His Asp Arg Gly Cys Ile Val Tyr Tyr
    395                 400                 405

gac cct ttg aag ttg att tct aaa ctt ggt gct aaa cac atc aag gat     4720
Asp Pro Leu Lys Leu Ile Ser Lys Leu Gly Ala Lys His Ile Lys Asp
410                 415                 420                 425

tgg gat cac tta gaa gag ttc aga aga tcc ctt tgt gat gtt gca aat     4768
Trp Asp His Leu Glu Glu Phe Arg Arg Ser Leu Cys Asp Val Ala Asn
                430                 435                 440

tcg ttg aac aac tgt gcg tat tac acg cag ttg gac gac gct gtg agt     4816
Ser Leu Asn Asn Cys Ala Tyr Tyr Thr Gln Leu Asp Asp Ala Val Ser
            445                 450                 455

gag gtc cat aaa acc gca ccc ccg ggt tcg tct gta tat aaa agt tta     4864
Glu Val His Lys Thr Ala Pro Pro Gly Ser Ser Val Tyr Lys Ser Leu
        460                 465                 470

gtt aaa tat ctg tcc gat aag gtt ctt ttt aga agt ttg ttt ata gat     4912
Val Lys Tyr Leu Ser Asp Lys Val Leu Phe Arg Ser Leu Phe Ile Asp
    475                 480                 485

ggc tct tgt taagggtaaa gtcaatatta atgagttcat agacttgtca             4961
Gly Ser Cys
490

aaatcagaaa aatttcttcc gtctatgttc acacctgtta agagtgtcat gatctccaag   5021

gttgataaga tattggttca tgaagatgaa tctttgtccg aagtcaattt actcaaaggt   5081

gtaaaactca ttgatggtgg ctatgtacat cttgctggtc ttgtggtgac aggtgaatgg   5141

aatttgccag ataattgtcg tggtggtgtc agtgtctgtt tggtcgataa gagaatggag   5201

agagcggacg aggcaactct tgcttcatac tataccgcag cggctaagaa aaggtttcag   5261

ttcaaagtcg ttccaaatta caacatcact accaaggacg cagaaaaggc agtttggcaa   5321

gtactagtta atattagaaa tgttaaaatt gctgcgggtt actgtccgct gtcattagaa   5381

tttgtgtcag tgtgtattgt ttataaaaat attataaaac tcggtttgag agagaaaatt   5441

acgagcgtca cggatggagg gcccatggaa ctatcagaag aagttgttga tgagttcatg   5501

gaagaagtcc cgatgtctgt aaggcttgca aaatttcgtt cgaagaccgg aaaaaagttt   5561

agtagtaaaa gtgagaataa tagtggtaat aataggccga aaccagacaa aaaccaaagg   5621

aagggaaagg gtttaaaagt tagggttgag aaggataatt taattgata atg aat tgg   5679
```

-continued

```
                                      Met Asn Trp
                                          495

aga ctt acg tcg ccg att cag att cgt att aaa tat tta aat atg tct     5727
Arg Leu Thr Ser Pro Ile Gln Ile Arg Ile Lys Tyr Leu Asn Met Ser
            500                 505                 510

tac aca atc gca act cca tcg caa ttt gtg ttt ttg tca tca gca tgg     5775
Tyr Thr Ile Ala Thr Pro Ser Gln Phe Val Phe Leu Ser Ser Ala Trp
            515                 520                 525

gcc gac cct ata gaa tta ata aat tta tgt act aat tca cta ggt aat     5823
Ala Asp Pro Ile Glu Leu Ile Asn Leu Cys Thr Asn Ser Leu Gly Asn
        530                 535                 540

cag ttc caa aca caa caa gct aga aca acc gtt caa cgg caa ttt agc     5871
Gln Phe Gln Thr Gln Gln Ala Arg Thr Thr Val Gln Arg Gln Phe Ser
    545                 550                 555

gaa gtg tgg aaa cct gtc cct caa gtc act gtt agg ttt cct gac agt     5919
Glu Val Trp Lys Pro Val Pro Gln Val Thr Val Arg Phe Pro Asp Ser
560                 565                 570                 575

ggt ttt aag gtg tat agg tac aat gcg gta cta gat cct cta gtt act     5967
Gly Phe Lys Val Tyr Arg Tyr Asn Ala Val Leu Asp Pro Leu Val Thr
            580                 585                 590

gct ttg tta gga gct ttc gat act aga aat agg att ata gaa gtc gaa     6015
Ala Leu Leu Gly Ala Phe Asp Thr Arg Asn Arg Ile Ile Glu Val Glu
            595                 600                 605

aat cag gcg aac ccg aca acc gcc gaa acg tta gac gct act cgt aga     6063
Asn Gln Ala Asn Pro Thr Thr Ala Glu Thr Leu Asp Ala Thr Arg Arg
        610                 615                 620

gta gat gac gca acg gtg gct ata agg agc gct ata aat aat tta gta     6111
Val Asp Asp Ala Thr Val Ala Ile Arg Ser Ala Ile Asn Asn Leu Val
    625                 630                 635

gta gaa ttg gtc aaa gga aca ggt ttg tac aat cag agc aca ttt gaa     6159
Val Glu Leu Val Lys Gly Thr Gly Leu Tyr Asn Gln Ser Thr Phe Glu
640                 645                 650                 655

agt gca tcc ggt tta caa tgg tcc tct gca cct gca tct tgagataatc      6208
Ser Ala Ser Gly Leu Gln Trp Ser Ser Ala Pro Ala Ser
            660                 665

gagatgctta aataacagat tgtgtctgca aacacacgtg gtacgtacga taacgtatag   6268

tgtttttccc tccacttaaa tcgaagggta gtgtcttgga gcgcgcggga caaatgtgta   6328

tggttcatac acatccgtag gcacgtaata aagcgaggga ttcgaattcc cccggaaccc   6388

ccggtagggg ccca                                                     6402


<210> SEQ ID NO 3
<211> LENGTH: 1116
<212> TYPE: PRT
<213> ORGANISM: unknown
<220> FEATURE:
<223> OTHER INFORMATION: ORF 1 (protein p126) of ToMSV strain VE484

<400> SEQUENCE: 3

Met Ala Tyr Thr Gln Thr Ala Thr Thr Ser Ala Leu Leu Asp Thr Val
1               5                   10                  15

Arg Gly Asn Asn Thr Leu Val Asn Asp Leu Ala Lys Arg Arg Leu Tyr
            20                  25                  30

Asp Thr Ala Val Asp Glu Phe Asn Ala Arg Asp Arg Arg Pro Lys Val
        35                  40                  45

Asn Phe Ser Lys Val Ile Ser Glu Glu Gln Thr Leu Ile Ala Thr Arg
    50                  55                  60

Ala Tyr Pro Glu Phe Gln Ile Thr Phe Tyr Asn Thr Gln Asn Ala Val
65                  70                  75                  80
```

-continued

```
His Ser Leu Ala Gly Gly Leu Arg Ser Leu Glu Leu Glu Tyr Leu Met
                85                  90                  95

Met Gln Ile Pro Tyr Gly Ser Leu Thr Tyr Asp Ile Gly Gly Asn Phe
            100                 105                 110

Ala Ser His Leu Phe Lys Gly Arg Ala Tyr Val His Cys Cys Met Pro
        115                 120                 125

Asn Leu Asp Val Arg Asp Ile Met Arg His Glu Gly Gln Lys Asp Ser
    130                 135                 140

Ile Glu Leu Tyr Leu Ser Arg Leu Glu Arg Gly Asn Lys Val Val Pro
145                 150                 155                 160

Asn Phe Gln Lys Glu Ala Leu Asp Arg Tyr Ala Glu Thr Pro Asp Glu
                165                 170                 175

Val Val Cys His Ser Thr Phe Gln Thr Cys Thr His Gln Gln Val Glu
            180                 185                 190

Asn Thr Gly Arg Val Tyr Ala Ile Ala Leu His Ser Ile Tyr Asp Ile
        195                 200                 205

Pro Ala Asp Glu Phe Gly Ala Ala Leu Leu Arg Lys Asn Val His Val
    210                 215                 220

Cys Tyr Ala Ala Phe His Phe Ser Glu Asn Leu Leu Leu Glu Asp Ser
225                 230                 235                 240

His Val Asn Leu Asp Glu Ile Asn Ala Cys Phe Ser Arg Asp Gly Asp
                245                 250                 255

Lys Leu Thr Phe Ser Phe Ala Ser Glu Ser Thr Leu Asn Tyr Cys His
            260                 265                 270

Ser Tyr Ser Asn Ile Leu Lys Tyr Val Cys Lys Thr Tyr Phe Pro Ala
        275                 280                 285

Ser Asn Arg Glu Val Tyr Met Lys Glu Phe Leu Val Thr Arg Val Asn
    290                 295                 300

Thr Trp Phe Cys Lys Phe Ser Arg Ile Asp Thr Phe Leu Leu Tyr Lys
305                 310                 315                 320

Gly Val Ala His Lys Gly Val Asn Ser Glu Gln Phe Tyr Ser Ala Met
                325                 330                 335

Glu Asp Ala Trp His Tyr Lys Lys Thr Leu Ala Met Cys Asn Ser Glu
            340                 345                 350

Arg Ile Leu Leu Glu Asp Ser Ser Ser Val Asn Tyr Trp Phe Pro Lys
        355                 360                 365

Met Arg Asp Met Val Ile Val Pro Leu Phe Asp Ile Ser Leu Asp Thr
    370                 375                 380

Ser Lys Arg Thr Arg Lys Glu Val Leu Val Ser Lys Asp Phe Val Phe
385                 390                 395                 400

Thr Val Leu Asn His Ile Arg Thr Tyr Gln Ala Lys Ala Leu Thr Tyr
                405                 410                 415

Ser Asn Val Leu Ser Phe Val Glu Ser Ile Arg Ser Arg Val Ile Ile
            420                 425                 430

Asn Gly Val Thr Ala Arg Ser Glu Trp Asp Val Asp Lys Ser Leu Leu
        435                 440                 445

Gln Ser Leu Ser Met Thr Phe Phe Leu His Thr Lys Leu Ala Val Leu
    450                 455                 460

Lys Asp Glu Leu Leu Ile Ser Lys Phe Ser Leu Gly Pro Lys Ser Val
465                 470                 475                 480

Ser Gln His Val Trp Asp Glu Ile Ser Leu Ala Phe Gly Asn Ala Phe
                485                 490                 495
```

-continued

```
Pro Ser Ile Lys Glu Arg Leu Leu Asn Arg Lys Leu Ile Lys Val Ser
            500                 505                 510

Gly Asp Ala Leu Glu Ile Arg Val Pro Asp Leu Tyr Val Thr Phe His
        515                 520                 525

Asp Arg Leu Val Thr Glu Tyr Lys Thr Ser Val Asp Met Pro Val Leu
    530                 535                 540

Asp Ile Arg Lys Arg Met Glu Glu Thr Glu Val Met Tyr Asn Ala Leu
545                 550                 555                 560

Ser Glu Leu Ser Val Leu Lys Glu Ser Asp Lys Phe Asp Ala Asp Val
                565                 570                 575

Phe Ser Arg Met Cys Gln Thr Leu Glu Val Asp Pro Met Thr Ala Ala
            580                 585                 590

Lys Val Ile Val Ala Val Met Ser Asn Glu Ser Gly Leu Thr Leu Thr
        595                 600                 605

Phe Glu Gln Pro Thr Glu Ala Asn Val Ala Leu Ala Leu Lys Asp Ser
    610                 615                 620

Glu Lys Ala Ser Glu Gly Ala Leu Val Val Thr Ser Arg Asp Val Glu
625                 630                 635                 640

Glu Pro Ser Met Lys Gly Ser Met Ala Arg Gly Glu Leu Gln Leu Ala
                645                 650                 655

Gly Leu Ser Gly Asp Gln Pro Glu Ser Ser Tyr Thr Arg Asn Glu Glu
            660                 665                 670

Ile Glu Ser Leu Glu Gln Phe His Met Ala Thr Ala Ser Ser Leu Ile
        675                 680                 685

Arg Lys Gln Met Ser Ser Ile Val Tyr Thr Gly Pro Ile Lys Val Gln
    690                 695                 700

Gln Met Lys Asn Phe Ile Asp Ser Leu Val Ala Ser Leu Ser Ala Ala
705                 710                 715                 720

Val Ser Asn Leu Val Lys Ile Leu Lys Asp Thr Ala Ala Ile Asp Leu
                725                 730                 735

Glu Thr Arg Gln Lys Phe Gly Val Leu Asp Val Ala Thr Lys Arg Trp
            740                 745                 750

Leu Ile Lys Pro Leu Ala Lys Asn His Ala Trp Gly Val Ile Glu Thr
        755                 760                 765

His Ala Arg Lys Tyr His Val Ala Leu Leu Glu Tyr Asp Glu His Gly
    770                 775                 780

Val Val Thr Cys Asp Ser Trp Arg Arg Val Ala Val Ser Ser Glu Ser
785                 790                 795                 800

Met Val Tyr Ser Asp Met Ala Lys Leu Arg Thr Leu Arg Arg Leu Leu
                805                 810                 815

Arg Asp Gly Glu Pro His Val Ser Ser Ala Lys Val Val Leu Val Asp
            820                 825                 830

Gly Val Pro Gly Cys Gly Lys Thr Lys Glu Ile Leu Ser Lys Val Asn
        835                 840                 845

Phe Glu Glu Asp Leu Ile Leu Val Pro Gly Lys Gln Ala Ala Glu Met
    850                 855                 860

Ile Lys Arg Arg Ala Asn Ala Ser Gly Ile Ile Gln Ala Thr Arg Asp
865                 870                 875                 880

Asn Val Arg Thr Val Asp Ser Phe Ile Met Asn Tyr Gly Lys Gly Thr
                885                 890                 895

Arg Cys Gln Phe Lys Arg Leu Phe Ile Asp Glu Gly Leu Met Leu His
            900                 905                 910

Thr Gly Cys Val Asn Phe Leu Val Ser Met Ser Leu Cys Glu Ile Ala
```

```
        915                 920                 925

Tyr Val Tyr Gly Asp Thr Gln Gln Ile Pro Tyr Ile Asn Arg Val Ser
    930                 935                 940

Gly Phe Pro Tyr Pro Ala His Phe Ala Lys Ile Glu Val Asp Glu Val
945                 950                 955                 960

Glu Thr Arg Arg Thr Thr Leu Arg Cys Pro Ala Asp Ile Thr His Tyr
                965                 970                 975

Leu Asn Arg Arg Tyr Glu Gly Tyr Val Met Cys Thr Ser Ser Val Lys
            980                 985                 990

Lys Ser Val Ser Gln Glu Met Val  Ser Gly Ala Ala Met  Ile Asn Pro
        995                 1000                1005

Val Ser  Lys Pro Leu Asn Gly  Lys Val Leu Thr Phe  Thr Gln Ser
    1010                1015                1020

Asp Lys  Glu Ala Leu Leu Ser  Arg Gly Tyr Thr Asp  Val His Thr
    1025                1030                1035

Val His  Glu Val Gln Gly Glu  Thr Tyr Ala Asp Val  Ser Leu Val
    1040                1045                1050

Arg Leu  Thr Pro Thr Pro Val  Ser Ile Ile Ala Gly  Asp Ser Pro
    1055                1060                1065

His Val  Leu Val Ala Leu Ser  Arg His Thr Gln Thr  Leu Lys Tyr
    1070                1075                1080

Tyr Thr  Val Val Met Asp Pro  Leu Val Ser Ile Ile  Arg Asp Leu
    1085                1090                1095

Glu Lys  Leu Ser Ser Tyr Leu  Leu Asp Met Tyr Lys  Val Asp Ala
    1100                1105                1110

Gly Thr  Gln
    1115


<210> SEQ ID NO 4
<211> LENGTH: 1609
<212> TYPE: PRT
<213> ORGANISM: unknown
<220> FEATURE:
<223> OTHER INFORMATION: ToMSV strain VE484 - ORF2 - protein p183
<220> FEATURE:
<221> NAME/KEY: misc_feature
<222> LOCATION: (1117)..(1117)
<223> OTHER INFORMATION: Xaa can be any naturally occurring amino acid

<400> SEQUENCE: 4

Met Ala Tyr Thr Gln Thr Ala Thr Thr Ser Ala Leu Leu Asp Thr Val
1               5                   10                  15

Arg Gly Asn Asn Thr Leu Val Asn Asp Leu Ala Lys Arg Arg Leu Tyr
            20                  25                  30

Asp Thr Ala Val Asp Glu Phe Asn Ala Arg Asp Arg Arg Pro Lys Val
        35                  40                  45

Asn Phe Ser Lys Val Ile Ser Glu Glu Gln Thr Leu Ile Ala Thr Arg
    50                  55                  60

Ala Tyr Pro Glu Phe Gln Ile Thr Phe Tyr Asn Thr Gln Asn Ala Val
65                  70                  75                  80

His Ser Leu Ala Gly Gly Leu Arg Ser Leu Glu Leu Glu Tyr Leu Met
                85                  90                  95

Met Gln Ile Pro Tyr Gly Ser Leu Thr Tyr Asp Ile Gly Gly Asn Phe
            100                 105                 110

Ala Ser His Leu Phe Lys Gly Arg Ala Tyr Val His Cys Cys Met Pro
        115                 120                 125
```

-continued

```
Asn Leu Asp Val Arg Asp Ile Met Arg His Glu Gly Gln Lys Asp Ser
    130                 135                 140

Ile Glu Leu Tyr Leu Ser Arg Leu Glu Arg Gly Asn Lys Val Val Pro
145                 150                 155                 160

Asn Phe Gln Lys Glu Ala Leu Asp Arg Tyr Ala Glu Thr Pro Asp Glu
                165                 170                 175

Val Val Cys His Ser Thr Phe Gln Thr Cys Thr His Gln Gln Val Glu
            180                 185                 190

Asn Thr Gly Arg Val Tyr Ala Ile Ala Leu His Ser Ile Tyr Asp Ile
        195                 200                 205

Pro Ala Asp Glu Phe Gly Ala Ala Leu Leu Arg Lys Asn Val His Val
    210                 215                 220

Cys Tyr Ala Ala Phe His Phe Ser Glu Asn Leu Leu Leu Glu Asp Ser
225                 230                 235                 240

His Val Asn Leu Asp Glu Ile Asn Ala Cys Phe Ser Arg Asp Gly Asp
                245                 250                 255

Lys Leu Thr Phe Ser Phe Ala Ser Glu Ser Thr Leu Asn Tyr Cys His
            260                 265                 270

Ser Tyr Ser Asn Ile Leu Lys Tyr Val Cys Lys Thr Tyr Phe Pro Ala
        275                 280                 285

Ser Asn Arg Glu Val Tyr Met Lys Glu Phe Leu Val Thr Arg Val Asn
    290                 295                 300

Thr Trp Phe Cys Lys Phe Ser Arg Ile Asp Thr Phe Leu Leu Tyr Lys
305                 310                 315                 320

Gly Val Ala His Lys Gly Val Asn Ser Glu Gln Phe Tyr Ser Ala Met
                325                 330                 335

Glu Asp Ala Trp His Tyr Lys Lys Thr Leu Ala Met Cys Asn Ser Glu
            340                 345                 350

Arg Ile Leu Leu Glu Asp Ser Ser Ser Val Asn Tyr Trp Phe Pro Lys
        355                 360                 365

Met Arg Asp Met Val Ile Val Pro Leu Phe Asp Ile Ser Leu Asp Thr
    370                 375                 380

Ser Lys Arg Thr Arg Lys Glu Val Leu Val Ser Lys Asp Phe Val Phe
385                 390                 395                 400

Thr Val Leu Asn His Ile Arg Thr Tyr Gln Ala Lys Ala Leu Thr Tyr
                405                 410                 415

Ser Asn Val Leu Ser Phe Val Glu Ser Ile Arg Ser Arg Val Ile Ile
            420                 425                 430

Asn Gly Val Thr Ala Arg Ser Glu Trp Asp Val Asp Lys Ser Leu Leu
        435                 440                 445

Gln Ser Leu Ser Met Thr Phe Phe Leu His Thr Lys Leu Ala Val Leu
    450                 455                 460

Lys Asp Glu Leu Leu Ile Ser Lys Phe Ser Leu Gly Pro Lys Ser Val
465                 470                 475                 480

Ser Gln His Val Trp Asp Glu Ile Ser Leu Ala Phe Gly Asn Ala Phe
                485                 490                 495

Pro Ser Ile Lys Glu Arg Leu Leu Asn Arg Lys Leu Ile Lys Val Ser
            500                 505                 510

Gly Asp Ala Leu Glu Ile Arg Val Pro Asp Leu Tyr Val Thr Phe His
        515                 520                 525

Asp Arg Leu Val Thr Glu Tyr Lys Thr Ser Val Asp Met Pro Val Leu
    530                 535                 540

Asp Ile Arg Lys Arg Met Glu Glu Thr Glu Val Met Tyr Asn Ala Leu
```

-continued

```
545                 550                 555                 560

Ser Glu Leu Ser Val Leu Lys Glu Ser Asp Lys Phe Asp Ala Asp Val
                565                 570                 575

Phe Ser Arg Met Cys Gln Thr Leu Glu Val Asp Pro Met Thr Ala Ala
            580                 585                 590

Lys Val Ile Val Ala Val Met Ser Asn Glu Ser Gly Leu Thr Leu Thr
        595                 600                 605

Phe Glu Gln Pro Thr Glu Ala Asn Val Ala Leu Ala Leu Lys Asp Ser
    610                 615                 620

Glu Lys Ala Ser Glu Gly Ala Leu Val Val Thr Ser Arg Asp Val Glu
625                 630                 635                 640

Glu Pro Ser Met Lys Gly Ser Met Ala Arg Gly Glu Leu Gln Leu Ala
                645                 650                 655

Gly Leu Ser Gly Asp Gln Pro Glu Ser Ser Tyr Thr Arg Asn Glu Glu
            660                 665                 670

Ile Glu Ser Leu Glu Gln Phe His Met Ala Thr Ala Ser Ser Leu Ile
        675                 680                 685

Arg Lys Gln Met Ser Ser Ile Val Tyr Thr Gly Pro Ile Lys Val Gln
    690                 695                 700

Gln Met Lys Asn Phe Ile Asp Ser Leu Val Ala Ser Leu Ser Ala Ala
705                 710                 715                 720

Val Ser Asn Leu Val Lys Ile Leu Lys Asp Thr Ala Ala Ile Asp Leu
                725                 730                 735

Glu Thr Arg Gln Lys Phe Gly Val Leu Asp Val Ala Thr Lys Arg Trp
            740                 745                 750

Leu Ile Lys Pro Leu Ala Lys Asn His Ala Trp Gly Val Ile Glu Thr
        755                 760                 765

His Ala Arg Lys Tyr His Val Ala Leu Leu Glu Tyr Asp Glu His Gly
    770                 775                 780

Val Val Thr Cys Asp Ser Trp Arg Arg Val Ala Val Ser Ser Glu Ser
785                 790                 795                 800

Met Val Tyr Ser Asp Met Ala Lys Leu Arg Thr Leu Arg Arg Leu Leu
                805                 810                 815

Arg Asp Gly Glu Pro His Val Ser Ser Ala Lys Val Val Leu Val Asp
            820                 825                 830

Gly Val Pro Gly Cys Gly Lys Thr Lys Glu Ile Leu Ser Lys Val Asn
        835                 840                 845

Phe Glu Glu Asp Leu Ile Leu Val Pro Gly Lys Gln Ala Ala Glu Met
    850                 855                 860

Ile Lys Arg Arg Ala Asn Ala Ser Gly Ile Ile Gln Ala Thr Arg Asp
865                 870                 875                 880

Asn Val Arg Thr Val Asp Ser Phe Ile Met Asn Tyr Gly Lys Gly Thr
                885                 890                 895

Arg Cys Gln Phe Lys Arg Leu Phe Ile Asp Glu Gly Leu Met Leu His
            900                 905                 910

Thr Gly Cys Val Asn Phe Leu Val Ser Met Ser Leu Cys Glu Ile Ala
        915                 920                 925

Tyr Val Tyr Gly Asp Thr Gln Gln Ile Pro Tyr Ile Asn Arg Val Ser
    930                 935                 940

Gly Phe Pro Tyr Pro Ala His Phe Ala Lys Ile Glu Val Asp Glu Val
945                 950                 955                 960

Glu Thr Arg Arg Thr Thr Leu Arg Cys Pro Ala Asp Ile Thr His Tyr
                965                 970                 975
```

-continued

```
Leu Asn Arg Arg Tyr Glu Gly Tyr Val Met Cys Thr Ser Ser Val Lys
            980                 985                 990

Lys Ser Val Ser Gln Glu Met Val  Ser Gly Ala Ala Met  Ile Asn Pro
        995                 1000                 1005

Val Ser  Lys Pro Leu Asn Gly  Lys Val Leu Thr Phe  Thr Gln Ser
    1010                 1015                 1020

Asp Lys  Glu Ala Leu Leu Ser  Arg Gly Tyr Thr Asp  Val His Thr
    1025                 1030                 1035

Val His  Glu Val Gln Gly Glu  Thr Tyr Ala Asp Val  Ser Leu Val
    1040                 1045                 1050

Arg Leu  Thr Pro Thr Pro Val  Ser Ile Ile Ala Gly  Asp Ser Pro
    1055                 1060                 1065

His Val  Leu Val Ala Leu Ser  Arg His Thr Gln Thr  Leu Lys Tyr
    1070                 1075                 1080

Tyr Thr  Val Val Met Asp Pro  Leu Val Ser Ile Ile  Arg Asp Leu
    1085                 1090                 1095

Glu Lys  Leu Ser Ser Tyr Leu  Leu Asp Met Tyr Lys  Val Asp Ala
    1100                 1105                 1110

Gly Thr  Gln Xaa Val Phe Lys  Gly Ser Asn Leu Phe  Val Ala Ala
    1115                 1120                 1125

Pro Lys  Thr Gly Asp Ile Ser  Asp Met Gln Phe Tyr  Tyr Asp Lys
    1130                 1135                 1140

Cys Leu  Pro Gly Asn Ser Thr  Met Leu Asn Asn Tyr  Asp Ala Val
    1145                 1150                 1155

Thr Met  Arg Leu Thr Asp Ile  Ser Leu Asn Val Lys  Asp Cys Ile
    1160                 1165                 1170

Leu Asp  Phe Ser Lys Ser Val  Ala Ala Pro Lys Asp  Pro Ile Lys
    1175                 1180                 1185

Pro Leu  Ile Pro Met Val Arg  Thr Ala Ala Glu Met  Pro Arg Gln
    1190                 1195                 1200

Thr Gly  Leu Leu Glu Asn Leu  Val Ala Met Ile Lys  Arg Asn Phe
    1205                 1210                 1215

Asn Ser  Pro Glu Leu Ser Gly  Ile Ile Asp Ile Glu  Asn Thr Ala
    1220                 1225                 1230

Ser Leu  Val Val Asp Lys Phe  Phe Asp Ser Tyr Leu  Leu Lys Glu
    1235                 1240                 1245

Lys Arg  Lys Pro Asn Lys Asn  Val Ser Leu Phe Cys  Arg Glu Ser
    1250                 1255                 1260

Leu Asn  Arg Trp Leu Glu Lys  Gln Glu Gln Val Thr  Ile Gly Gln
    1265                 1270                 1275

Leu Ala  Asp Phe Asp Phe Val  Asp Leu Pro Ala Val  Asp Gln Tyr
    1280                 1285                 1290

Arg His  Met Ile Lys Ala Gln  Pro Lys Gln Lys Leu  Asp Thr Ser
    1295                 1300                 1305

Ile Gln  Ser Glu Tyr Pro Ala  Leu Gln Thr Ile Val  Tyr His Ser
    1310                 1315                 1320

Lys Lys  Ile Asn Ala Ile Phe  Gly Pro Leu Phe Ser  Glu Leu Thr
    1325                 1330                 1335

Arg Gln  Met Leu Glu Ser Ile  Asp Ser Ser Lys Phe  Leu Phe Phe
    1340                 1345                 1350

Thr Arg  Lys Thr Pro Ala Gln  Ile Glu Asp Phe Phe  Gly Asp Leu
    1355                 1360                 1365
```

Asp Ser His Val Pro Met Asp Ile Leu Glu Leu Asp Ile Ser Lys
1370 1375 1380

Tyr Asp Lys Ser Gln Asn Glu Phe His Cys Ala Val Glu Tyr Glu
1385 1390 1395

Ile Trp Arg Arg Leu Gly Leu Glu Asp Phe Leu Gly Glu Val Trp
1400 1405 1410

Lys Gln Gly His Arg Lys Thr Thr Leu Lys Asp Tyr Thr Ala Gly
1415 1420 1425

Ile Lys Thr Cys Leu Trp Tyr Gln Arg Lys Ser Gly Asp Val Thr
1430 1435 1440

Thr Phe Ile Gly Asn Thr Val Ile Ile Ala Ala Cys Leu Ala Ser
1445 1450 1455

Met Leu Pro Met Glu Lys Ile Ile Lys Gly Ala Phe Cys Gly Asp
1460 1465 1470

Asp Ser Leu Leu Tyr Phe Pro Lys Gly Cys Glu Phe Pro Asp Ile
1475 1480 1485

Gln His Thr Ala Asn Leu Met Trp Asn Phe Glu Ala Lys Leu Phe
1490 1495 1500

Arg Lys Gln Tyr Gly Tyr Phe Cys Gly Arg Tyr Val Ile His His
1505 1510 1515

Asp Arg Gly Cys Ile Val Tyr Tyr Asp Pro Leu Lys Leu Ile Ser
1520 1525 1530

Lys Leu Gly Ala Lys His Ile Lys Asp Trp Asp His Leu Glu Glu
1535 1540 1545

Phe Arg Arg Ser Leu Cys Asp Val Ala Asn Ser Leu Asn Asn Cys
1550 1555 1560

Ala Tyr Tyr Thr Gln Leu Asp Asp Ala Val Ser Glu Val His Lys
1565 1570 1575

Thr Ala Pro Pro Gly Ser Ser Val Tyr Lys Ser Leu Val Lys Tyr
1580 1585 1590

Leu Ser Asp Lys Val Leu Phe Arg Ser Leu Phe Ile Asp Gly Ser
1595 1600 1605

Cys

<210> SEQ ID NO 5
<211> LENGTH: 266
<212> TYPE: PRT
<213> ORGANISM: unknown
<220> FEATURE:
<223> OTHER INFORMATION: ToMSV VE484 - ORF3 - Movement Protein

<400> SEQUENCE: 5

Met Ala Leu Val Lys Gly Lys Val Asn Ile Asn Glu Phe Ile Asp Leu
1 5 10 15

Ser Lys Ser Glu Lys Phe Leu Pro Ser Met Phe Thr Pro Val Lys Ser
20 25 30

Val Met Ile Ser Lys Val Asp Lys Ile Leu Val His Glu Asp Glu Ser
35 40 45

Leu Ser Glu Val Asn Leu Leu Lys Gly Val Lys Leu Ile Asp Gly Gly
50 55 60

Tyr Val His Leu Ala Gly Leu Val Val Thr Gly Glu Trp Asn Leu Pro
65 70 75 80

Asp Asn Cys Arg Gly Gly Val Ser Val Cys Leu Val Asp Lys Arg Met
85 90 95

Glu Arg Ala Asp Glu Ala Thr Leu Ala Ser Tyr Tyr Thr Ala Ala Ala

```
            100                 105                 110

Lys Lys Arg Phe Gln Phe Lys Val Val Pro Asn Tyr Asn Ile Thr Thr
        115                 120                 125

Lys Asp Ala Glu Lys Ala Val Trp Gln Val Leu Val Asn Ile Arg Asn
    130                 135                 140

Val Lys Ile Ala Ala Gly Tyr Cys Pro Leu Ser Leu Glu Phe Val Ser
145                 150                 155                 160

Val Cys Ile Val Tyr Lys Asn Ile Ile Lys Leu Gly Leu Arg Glu Lys
                165                 170                 175

Ile Thr Ser Val Thr Asp Gly Gly Pro Met Glu Leu Ser Glu Glu Val
            180                 185                 190

Val Asp Glu Phe Met Glu Glu Val Pro Met Ser Val Arg Leu Ala Lys
        195                 200                 205

Phe Arg Ser Lys Thr Gly Lys Lys Phe Ser Ser Lys Ser Glu Asn Asn
    210                 215                 220

Ser Gly Asn Asn Arg Pro Lys Pro Asp Lys Asn Gln Arg Lys Gly Lys
225                 230                 235                 240

Gly Leu Lys Val Arg Val Glu Lys Asp Asn Leu Ile Asp Asn Glu Leu
                245                 250                 255

Glu Thr Tyr Val Ala Asp Ser Asp Ser Tyr
            260                 265
```

<210> SEQ ID NO 6
<211> LENGTH: 176
<212> TYPE: PRT
<213> ORGANISM: unknown
<220> FEATURE:
<223> OTHER INFORMATION: ORF4 - Coat Protein of ToMSV VE484

<400> SEQUENCE: 6

```
Met Asn Trp Arg Leu Thr Ser Pro Ile Gln Ile Arg Ile Lys Tyr Leu
1               5                   10                  15

Asn Met Ser Tyr Thr Ile Ala Thr Pro Ser Gln Phe Val Phe Leu Ser
            20                  25                  30

Ser Ala Trp Ala Asp Pro Ile Glu Leu Ile Asn Leu Cys Thr Asn Ser
        35                  40                  45

Leu Gly Asn Gln Phe Gln Thr Gln Gln Ala Arg Thr Thr Val Gln Arg
    50                  55                  60

Gln Phe Ser Glu Val Trp Lys Pro Val Pro Gln Val Thr Val Arg Phe
65                  70                  75                  80

Pro Asp Ser Gly Phe Lys Val Tyr Arg Tyr Asn Ala Val Leu Asp Pro
                85                  90                  95

Leu Val Thr Ala Leu Leu Gly Ala Phe Asp Thr Arg Asn Arg Ile Ile
            100                 105                 110

Glu Val Glu Asn Gln Ala Asn Pro Thr Thr Ala Glu Thr Leu Asp Ala
        115                 120                 125

Thr Arg Arg Val Asp Asp Ala Thr Val Ala Ile Arg Ser Ala Ile Asn
    130                 135                 140

Asn Leu Val Val Glu Leu Val Lys Gly Thr Gly Leu Tyr Asn Gln Ser
145                 150                 155                 160

Thr Phe Glu Ser Ala Ser Gly Leu Gln Trp Ser Ser Ala Pro Ala Ser
                165                 170                 175
```

<210> SEQ ID NO 7
<211> LENGTH: 23
<212> TYPE: DNA

-continued

```
<213> ORGANISM: unknown
<220> FEATURE:
<223> OTHER INFORMATION: primer Tob-uni 1

<400> SEQUENCE: 7

atttaagtgg asggaaaavc act                                                23


<210> SEQ ID NO 8
<211> LENGTH: 20
<212> TYPE: DNA
<213> ORGANISM: unknown
<220> FEATURE:
<223> OTHER INFORMATION: primer Tob-uni 2

<400> SEQUENCE: 8

gtygttgatg agttcrtgga                                                    20


<210> SEQ ID NO 9
<211> LENGTH: 29
<212> TYPE: DNA
<213> ORGANISM: unknown
<220> FEATURE:
<223> OTHER INFORMATION: primer Tobamo F

<400> SEQUENCE: 9

gwcgcsgakt ckgattcgtw ttaaatatg                                          29


<210> SEQ ID NO 10
<211> LENGTH: 17
<212> TYPE: DNA
<213> ORGANISM: unknown
<220> FEATURE:
<223> OTHER INFORMATION: primer tobamo R

<400> SEQUENCE: 10

tgggccscta ccsgsgg                                                       17
```